United States Patent
Oved et al.

(10) Patent No.: US 11,006,833 B2
(45) Date of Patent: May 18, 2021

(54) MEDICAL OPTICAL EXAMINATION INSTRUMENT

(71) Applicant: FRESH POND VENTURES LLC, Belmont, MA (US)

(72) Inventors: Dror Oved, Austin, TX (US); Kapriel Karagozyan, Belmont, MA (US)

(73) Assignee: FRESH POND VENTURES LLC, Belmont, MA (US)

( * ) Notice: Subject to any disclaimer, the term of this patent is extended or adjusted under 35 U.S.C. 154(b) by 0 days.

(21) Appl. No.: 15/830,771

(22) Filed: Dec. 4, 2017

(65) Prior Publication Data

US 2018/0084999 A1 Mar. 29, 2018

Related U.S. Application Data

(63) Continuation of application No. PCT/IL2016/051297, filed on Dec. 5, 2016, which is
(Continued)

(51) Int. Cl.
*A61B 1/227* (2006.01)
*A61B 5/00* (2006.01)
(Continued)

(52) U.S. Cl.
CPC ........ *A61B 5/0035* (2013.01); *A61B 1/00004* (2013.01); *A61B 1/00013* (2013.01);
(Continued)

(58) Field of Classification Search
CPC ...... A61B 1/00045–0005; A61B 1/163; A61B 1/227; A61B 3/12–1208; A61B 3/158
See application file for complete search history.

(56) References Cited

U.S. PATENT DOCUMENTS 5,239,984 A 8/1993 Cane et al.
6,319,199 B1 11/2001 Sheehan et al.
(Continued)

FOREIGN PATENT DOCUMENTS

EP 2578140 A1 4/2013
WO 02/056756 A2 7/2002
(Continued)

OTHER PUBLICATIONS

An International Preliminary Report on Patentability dated Dec. 4, 2018, which issued during the prosecution of Applicant's PCT/IL2016/051297.
(Continued)

*Primary Examiner* — Eduardo C Robert
*Assistant Examiner* — Steven J Cotroneo
(74) *Attorney, Agent, or Firm* — Sughrue Mion, PLLC

(57) ABSTRACT

A multifunctional medical optical examination instrument including a hand-holdable portion, at least an optical examination head portion mountable on the hand-holdable portion and including at least optical examination and non-digitized viewing optics and image digitization, storage and transmission circuitry included in at least one of the hand-holdable portion and the at least optical examination head portion, the image digitization, storage and transmission circuitry being arranged to receive an image from at least a portion of the at least optical examination and non-digitized viewing optics.

25 Claims, 14 Drawing Sheets

Related U.S. Application Data a continuation-in-part of application No. PCT/IL2016/050574, filed on Jun. 2, 2016.

(60) Provisional application No. 62/171,665, filed on Jun. 5, 2015.

(51) Int. Cl.
| | | |
|---|---|---|
| *A61B 1/00* | (2006.01) | |
| *A61B 3/12* | (2006.01) | |
| *A61B 3/00* | (2006.01) | |
| *A61B 3/18* | (2006.01) | |
| *A61B 1/04* | (2006.01) | |

(52) U.S. Cl.
CPC ...... *A61B 1/00016* (2013.01); *A61B 1/00108* (2013.01); *A61B 1/227* (2013.01); *A61B 3/0025* (2013.01); *A61B 3/1208* (2013.01); *A61B 3/18* (2013.01); *A61B 5/0077* (2013.01); *A61B 1/0002* (2013.01); *A61B 1/00009* (2013.01); *A61B 1/00105* (2013.01); *A61B 1/00163* (2013.01); *A61B 1/04* (2013.01); *A61B 2562/0233* (2013.01)

(56) References Cited

U.S. PATENT DOCUMENTS

| | | | | |
|---|---|---|---|---|
| 6,636,696 B2* | 10/2003 | Saito | .................... | G03B 29/00 351/206 |
| 7,784,940 B2* | 8/2010 | Goldfain | ................ | A61B 3/158 351/200 |
| 10,098,529 B2* | 10/2018 | Gao | ........................ | A61B 1/227 |
| 2003/0157464 A1* | 8/2003 | Tanassi | .................... | A61B 3/12 434/81 |
| 2003/0208125 A1* | 11/2003 | Watkins | .................... | A61B 3/12 600/473 |
| 2005/0027169 A1* | 2/2005 | Goldfain | ............ | A61B 1/00188 600/200 |
| 2005/0110949 A1* | 5/2005 | Goldfain | ................ | A61B 3/158 351/206 |
| 2005/0234300 A1* | 10/2005 | Farrell | .................... | A61B 3/145 600/167 |
| 2007/0211605 A1* | 9/2007 | Sakamoto | ................ | G02B 9/12 369/112.24 |
| 2009/0312638 A1* | 12/2009 | Bartlett | .................... | A61B 5/00 600/443 |
| 2010/0094082 A1 | 4/2010 | Iinuma et al. | | |
| 2011/0137118 A1* | 6/2011 | Huang | .................... | A61B 1/227 600/109 |
| 2013/0102359 A1 | 4/2013 | Ho | | |
| 2013/0128223 A1* | 5/2013 | Wood | .................... | A61B 5/0077 351/206 |
| 2013/0267784 A1 | 10/2013 | Andreassen et al. | | |
| 2015/0126810 A1 | 5/2015 | Wood et al. | | |
| 2015/0223678 A1* | 8/2015 | Goldfain | ................ | A61B 1/227 600/200 |
| 2015/0238071 A1* | 8/2015 | Hua | ........................ | A61B 1/07 600/109 |
| 2015/0250381 A1* | 9/2015 | Bedard | .................. | A61B 1/227 600/200 |
| 2018/0168440 A1* | 6/2018 | Das | ........................ | A61B 5/6817 |

FOREIGN PATENT DOCUMENTS

| | | |
|---|---|---|
| WO | 2016/193984 | 12/2016 |
| WO | 2017/208220 | 12/2017 |

OTHER PUBLICATIONS

European Search Report dated Dec. 10, 2018, which issued during the prosecution of Applicant's European App No. 16802698.7.

U.S. Appl. No. 62/171,665, filed Jun. 5, 2015.

An International Search Report and a Written Opinion both dated Jul. 19, 2017, which issued during the prosecution of Applicant's PCT/IL2016/051297.

An International Search Report and a Written Opinion both dated Nov. 15, 2016, which issued during the prosecution of Applicant's PCT/IL2016/050574.

An International Preliminary Report on Patentability dated Dec. 5, 2017, which issued during the prosecution of Applicant's PCT/IL2016/050574.

* cited by examiner

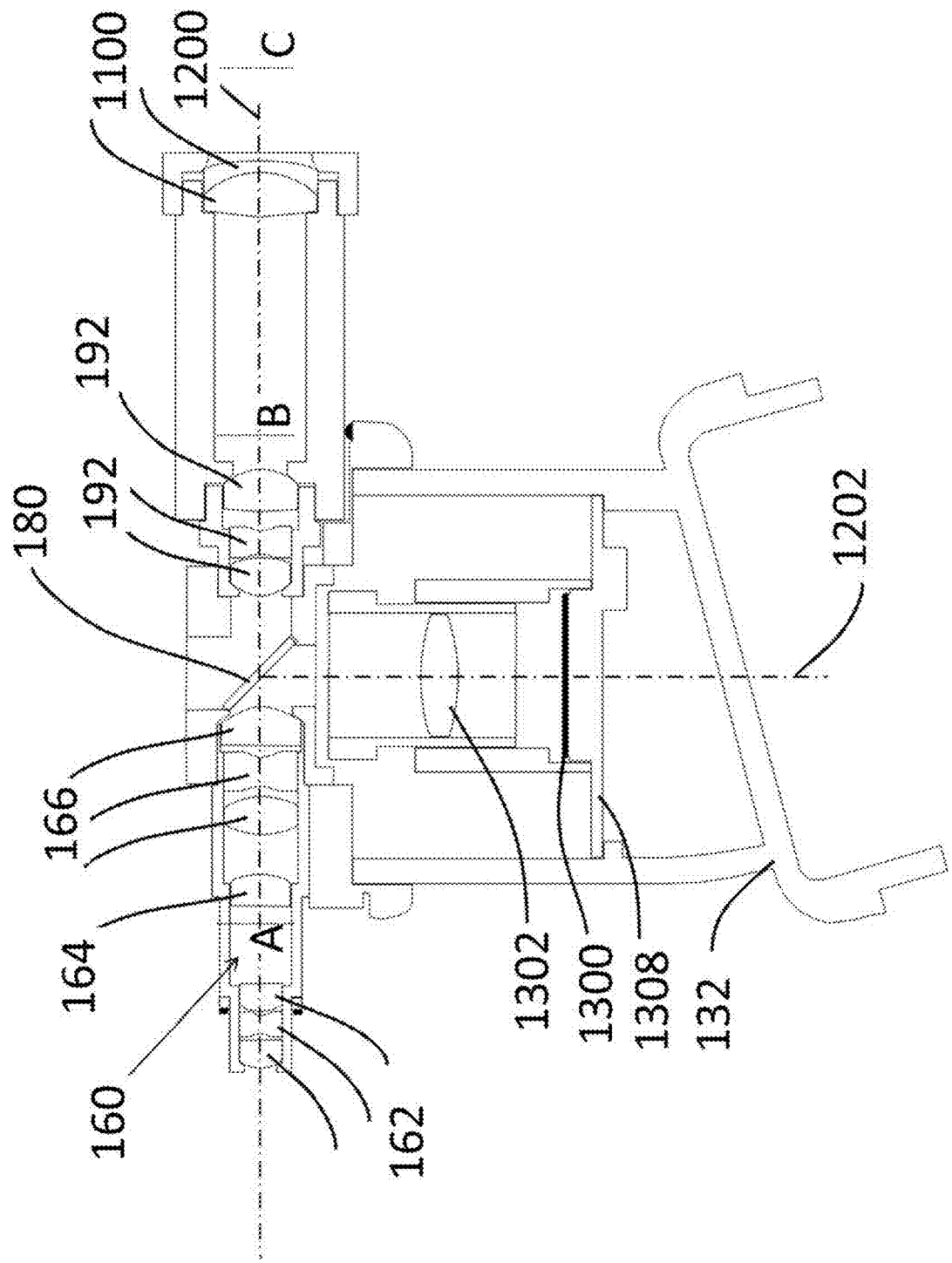

MEDICAL OPTICAL EXAMINATION INSTRUMENT

REFERENCE TO RELATED APPLICATIONS

This application is a continuation of PCT Patent Application No. PCT/IL2016/051297, entitled MEDICAL OPTICAL EXAMINATION INSTRUMENT filed Dec. 5, 2016, which is a continuation-in-part of PCT Patent Application No. PCT/IL2016/050574, entitled MEDICAL OPTICAL EXAMINATION INSTRUMENT filed Jun. 2, 2016, which claims priority of U.S. Provisional Patent Application No. 62/171,665, entitled A DIAGNOSTIC MEDICAL IMAGING INSTRUMENT SET WITH MULTIPLE AXIS OPTICAL SYSTEM, filed Jun. 5, 2015.

FIELD OF THE INVENTION

The present invention relates generally to medical examination instruments and more particularly to medical optical examination instruments.

BACKGROUND OF THE INVENTION

Various types of medical optical examination instruments are known in the art.

SUMMARY OF THE INVENTION

The present invention seeks to provide an improved medical optical examination instrument having both analogue and digital imaging functionalities.

There is thus provided in accordance with a preferred embodiment of the present invention a multifunctional medical optical examination instrument including a hand-holdable portion, at least an optical examination head portion mountable on the hand-holdable portion and including at least optical examination and non-digitized viewing optics and image digitization, storage and transmission circuitry included in at least one of the hand-holdable portion and the at least optical examination head portion, the image digitization, storage and transmission circuitry being arranged to receive an image from at least a portion of the at least optical examination and non-digitized viewing optics.

Preferably, the image digitization, storage and transmission circuitry is operative to receive an image from the at least portion of the at least optical examination and non-digitized viewing optics at least partially simultaneously with the image being viewable by a user via the optical examination and non-digitized viewing optics.

Preferably, the instrument also includes a lens system receiving the image from the at least portion of the at least optical examination and non-digitized viewing optics and relaying the image received from the at least portion of the at least optical examination and non-digitized viewing optics to the image digitization, storage and transmission circuitry.

Preferably, the image viewable by the user via the optical examination and non-digitized viewing optics and the image received by the image digitization, storage and transmission circuitry are each in focus, without requiring focusing adjustments to the optical examination and non-digitized viewing optics.

Preferably, the optical examination and non-digitized viewing optics do not include adjustable focusing elements.

Preferably, the image viewable by the user via the optical examination and non-digitized viewing optics and the image received by the image digitization, storage and transmission circuitry are each in focus, without requiring focusing adjustments to the optical examination and non-digitized viewing optics and to the lens system, wherein the optical examination and non-digitized viewing optics and the lens system do not include adjustable focusing elements.

In accordance with a preferred embodiment of the present invention, the lens system includes a single lens. Alternatively, the lens system includes a group of lenses.

Preferably, the instrument has a focal depth of between 0-100 mm.

Preferably, the image digitization, storage and transmission circuitry is included in the hand-holdable portion.

Preferably, the optical examination and non-digitized viewing optics include a beam splitter.

Preferably, the head portion includes an optical passage extending therethrough, the optical passage including a distal end defining a distal opening and a proximal end defining a proximal opening, the distal opening being adapted for positioning in proximity to a target to be examined, the proximal opening being adapted for positioning in proximity to an eye of the user, the beam splitter being located within the optical passage between the distal and proximal ends thereof.

Preferably, the distal opening, the proximal opening and the beam splitter are mutually optically aligned along a first optical pathway and at least a part of the image digitization, storage and transmission circuitry and the beam splitter are mutually optically aligned along a second optical pathway, the first and second optical pathways being mutually angled.

Preferably, at least part of the image digitization, storage and transmission circuitry includes a digital sensor.

Preferably, the beam splitter is separated from the digital sensor by a distance of between 1-25 cm.

Preferably, at least one of the first and the second optical pathways is linear.

Additionally or alternatively, at least one of the first and the second optical pathways is non-linear.

In accordance with a preferred embodiment of the present invention, the instrument also includes a multiplicity of optical elements optically aligned along the first optical pathway, the multiplicity of optical elements including an aperture stop formed by the distal opening, a first train of lenses located behind the aperture stop and operative to form an image of the target, a second lens spaced apart from the first train of lenses and optically aligned therewith, the second lens being operative to relay an image of the aperture stop, a third train of lenses spaced apart from the second lens in a direction away from the distal opening and optically aligned with the second lens, the third train of lenses being operative to collimate light passing therethrough and an eye piece located adjacent to the third train of lenses and including an anterior lens arrangement and a posterior lens arrangement, the anterior lens arrangement being operative to receive collimated light from the third train of lenses and produce an image at a finite distance therefrom, the posterior lens arrangement being located at the proximal opening and being operative to form an image of the target viewable by the user.

In accordance with another preferred embodiment of the present invention, the instrument also includes a multiplicity of optical elements optically aligned along the first optical pathway, the multiplicity of optical elements comprising a first train of lenses operative to form an intermediate image of the target and a second train of lenses spaced apart from the first train of lenses, the second train of lenses being operative to receive the intermediate image and focus the intermediate image to form an image of the target viewable by the user.

Preferably, the instrument also includes illumination sources located in the optical examination head portion.

Preferably, the instrument is connectable to an external computing device, the image digitization, storage and transmission circuitry being operative to transfer the image to the external computing device.

Preferably, the image includes at least one of a digital still image and a digital video frame.

Preferably, the image digitization, storage and transmission circuitry is operative to store at least one of the digital still image and the digital video frame.

Preferably, the image digitization, storage and transmission circuitry is operative to perform live video streaming of the image to the external computing device in real time.

Preferably, the transfer is wireless. Alternatively, the transfer is wired.

Preferably, the external computing device includes a non-transitory computer readable medium having stored thereupon computer instructions including code segments having the following functionalities: image processing functionality, for receiving and processing the image generated by the image digitization, storage and transmission circuitry, image display functionality for displaying the image processed by the image processing functionality, image capture functionality for capturing the image displayed by the image display functionality and image management functionality for managing the image captured by the image capture functionality.

Preferably, the functionalities also include remote control functionality for remote control of the image digitization, storage and transmission circuitry.

Preferably, the functionalities also include image analysis functionality for analyzing the image captured by the image capture functionality.

Preferably, the image digitization storage and transmission circuitry includes at least one antenna.

Preferably, the hand-holdable portion includes a connector port.

Preferably, the instrument also includes a power supply located in the hand-holdable portion.

Preferably, the power supply includes a battery.

Preferably, the optical examination head portion includes an otoscope head portion, the image digitization, storage and transmission circuitry being arranged to receive an image from at least a portion of the at least optical examination and non-digitized viewing optics of the otoscope head portion, when the otoscope head portion is mounted on the hand-holdable portion.

Alternatively, the optical examination head portion includes a dermatoscope head portion, the image digitization, storage and transmission circuitry being arranged to receive an image from at least a portion of the at least optical examination and non-digitized viewing optics of the dermatoscope head portion, when the dermatoscope head portion is mounted on the hand-holdable portion.

Further alternatively, the optical examination head portion includes an ophthalmoscope head portion, the image digitization, storage and transmission circuitry being arranged to receive an image from at least a portion of the at least optical examination and non-digitized viewing optics of the ophthalmoscope head portion, when the ophthalmoscope head portion is mounted on the hand-holdable portion.

Still further alternatively, the optical examination head portion includes a general purpose examination head portion, the image digitization, storage and transmission circuitry being arranged to receive an image from at least a portion of the at least optical examination and non-digitized viewing optics of the general purpose examination head portion, when the general purpose examination head portion is mounted on the hand-holdable portion.

There is further provided in accordance with a preferred embodiment of the present invention a multifunctional medical optical examination instrument set, including a plurality of optical examination head portions according to preferred embodiments of the present invention, the plurality of optical examination head portions being interchangeably and replaceably mountable on the hand-holdable portion.

There is additionally provided in accordance with another preferred embodiment of the present invention an optical arrangement for incorporation in an otoscope including an aperture stop formed by a distal opening of the otoscope, a first train of lenses located behind the aperture stop and operative to form an image of a target, a second lens spaced apart from the first train of lenses and optically aligned therewith, the second lens being operative to relay an image of the aperture stop, a third train of lenses spaced apart from the second lens in a direction away from the distal opening and optically aligned with the second lens, the third train of lenses being operative to collimate light passing therethrough and an eye piece located adjacent to the third train of lenses and including an anterior lens arrangement and a posterior lens arrangement, the anterior lens arrangement being operative to receive collimated light from the third train of lenses and produce an image at a finite distance therefrom, the posterior lens arrangement being located at a proximal opening of the otoscope and being operative to form an image of the target viewable by a user.

There is also provided in accordance with still another preferred embodiment of the present invention a multifunctional medical optical examination instrument including optical examination and non-digitized viewing optics providing an image of a target and image digitization, storage and transmission circuitry receiving the image from at least a portion of the optical examination and non-digitized viewing optics at least partially simultaneously with the image being viewable by a user via the optical examination and non-digitized viewing optics, at least the optical examination and non-digitized viewing optics being configured such that the image received by the image digitization, storage and transmission circuitry and the image viewable by the user via the optical examination and non-digitized viewing optics are at least partially simultaneously in focus when the target is located at any one of a range of locations within a focal depth of the instrument.

Preferably, the instrument also includes a lens system receiving the image from the at least portion of the optical examination and non-digitized viewing optics and relaying the image received from the at least portion of the at least optical examination and non-digitized viewing optics to the image digitization, storage and transmission circuitry.

In accordance with a preferred embodiment of the present invention, the optical examination and non-digitized viewing optics include a beam splitter, a first train of lenses spaced apart from the beam splitter and operative to form an intermediate image of the target and a second train of lenses spaced apart from the first train of lenses, the second train of lenses being operative to receive the intermediate image and focus the intermediate image to form the image of the target viewable by the user.

Preferably, the image digitization, storage and transmission circuitry includes a digital sensor, the digital sensor and the beam splitter being mutually optically aligned along an optical pathway.

Preferably, the digital sensor is spaced apart from the beam splitter along the optical pathway by a distance of 1-25 cm.

Preferably, the optical pathway is linear. Alternatively, the optical pathway is non-linear.

Preferably, the focal depth is less than or equal to 100 mm.

Preferably, the image received by the image digitization, storage and transmission circuitry and the image viewable by the user via the optical examination and non-digitized viewing optics are at least partially simultaneously in focus without requiring focusing adjustments to at least one of the optical examination and non-digitized viewing optics and to the lens system.

Preferably, at least one of the optical examination and non-digitized viewing optics and the lens system do not include adjustable focusing elements.

Preferably, the instrument includes a hand-holdable portion and a head portion supported by the hand-holdable portion, the optical examination and non-digitized viewing optics being included in the head portion, the image digitization, storage and transmission circuitry being included in at least one of the head portion and the hand-holdable portion.

BRIEF DESCRIPTION OF THE DRAWINGS

The present invention will be understood and appreciated more fully from the following detailed description, taken in conjunction with the drawings in which:

FIGS. 2 and 3 are simplified enlarged cross-sectional view illustrations of respective portions of a medical optical examination instrument of the type shown in FIGS. 1A and 1B;

DETAILED DESCRIPTION OF PREFERRED EMBODIMENTS

Figure 1A:
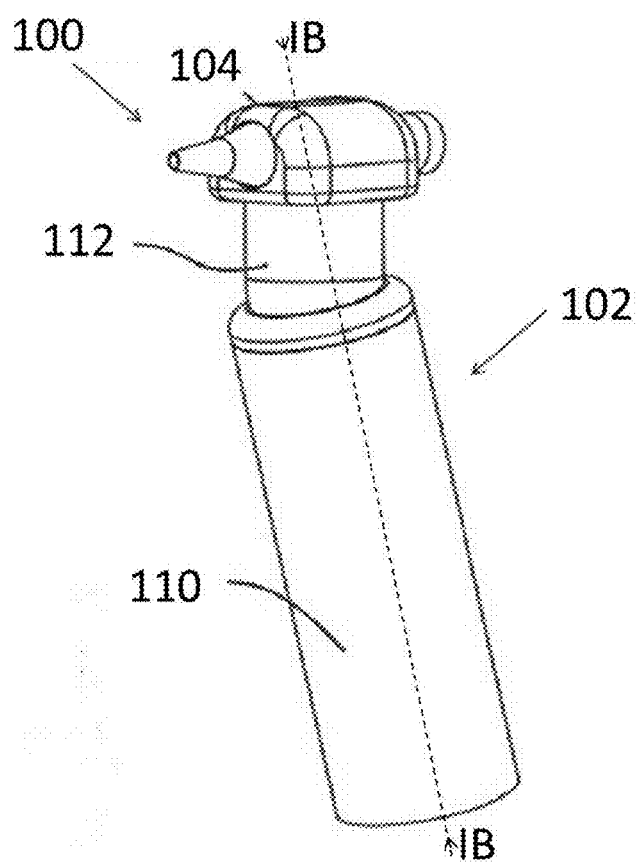
FIGS. 1A and 1B are simplified respective schematic external perspective and cross-sectional view illustrations of a medical optical examination instrument constructed and operative in accordance with a preferred embodiment of the present invention.
Figure 1B:
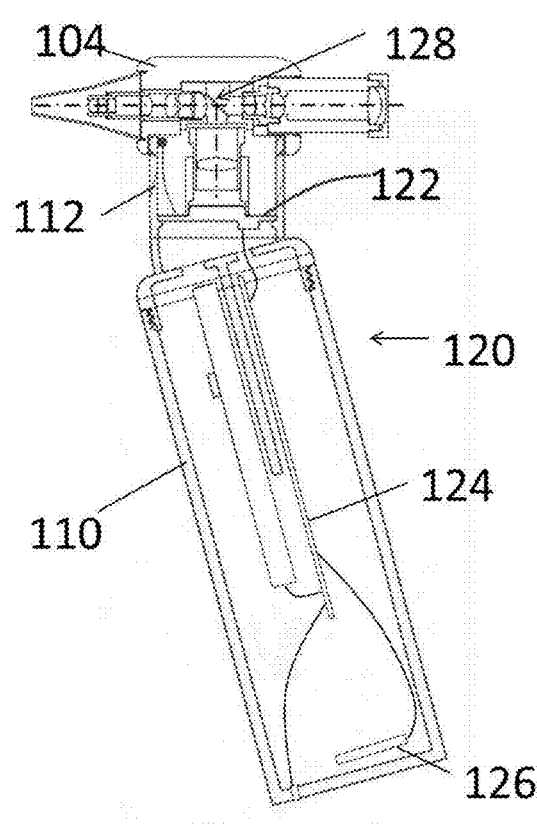

Reference is now made to FIGS. 1A and 1B, which are simplified respective schematic external perspective and cross-sectional view illustrations of a medical optical examination instrument constructed and operative in accordance with a preferred embodiment of the present invention.

As seen in FIGS. 1A and 1B, there is provided a medical optical examination instrument 100, preferably including a hand-holdable portion 102 forming a handle of instrument 100 and at least an optical examination head portion 104 mountable on hand-holdable portion 102. Here, by way of example only, optical examination head portion 104 is seen to be embodied as an otoscope head portion 104, such that medical optical examination instrument 100 functions as an otoscope. It is appreciated, however, that optical examination head portion 104 is not limited to being an otoscope head portion and that medical optical examination instrument 100 is correspondingly not limited to functioning as an otoscope. Rather, instrument 100 may be embodied as one of a variety of types of medical optical examination instruments, including an ophthalmoscope or dermatoscope, as will be detailed henceforth.

Hand-holdable portion 102 may include a body portion 110 and a neck portion 112, on which neck portion 112 head portion 104 is preferably mounted. Alternatively, hand-holdable portion 102 may have a variety of other ergonomic configurations, not necessarily including a distinct neck segment of the type of neck portion 112.

As seen most clearly in FIG. 1B, instrument 100 preferably includes image digitization, storage and transmission circuitry generally designated by a reference number 120 and included in at least one of hand-holdable portion 102 and optical examination head portion 104. Here, by way of example, image digitization, storage and transmission circuitry 120 is shown to be entirely located in hand-holdable portion 102. It is appreciated, however, that image digitization, storage and transmission circuitry 120 may alternatively be entirely located in head portion 104 or distributed between hand-holdable portion 102 and head portion 104 depending on the design requirements of the optical examination instrument of the present invention.

Image digitization, storage and transmission circuitry 120 may comprise an image digitization component 122, an image storage component 124 and an image transmission component 126, by way of example. Further details concerning the structure and operation of image digitization, storage and transmission circuitry 120 will be provided henceforth with reference to FIGS. 4A and 4B.

Optical examination head portion 104 preferably includes at least optical examination and non-digitized viewing optics generally designated by a reference number 128. Optical examination and non-digitized viewing optics 128 are preferably operative to provide an image of a target, such as the ear canal and tympanic membrane of a patient, in the case that optical examination head portion 104 comprises an otoscope head portion. Further details concerning the structure and operation of optical examination and non-digitized viewing optics 128 are provided henceforth with reference to FIGS. 2 and 3.

It is a particular feature of a preferred embodiment of the present invention that image digitization, storage and transmission circuitry 120 is arranged to receive an image from at least a portion of at least optical examination and non-digitized viewing optics 128 when head portion 104 is mounted on hand-holdable portion 102.

Receipt of an image from optics 128 in head portion 104 by image digitization, storage and transmission circuitry 120 preferably occurs at least partially simultaneously with the image being viewable in a non-digitized form by a user via optical examination and non-digitized viewing optics 128. It is appreciated that instrument 100 thus constitutes a multifunctional instrument, allowing a user to view an image captured thereby in a non-digitized, analogue fashion in addition to and preferably simultaneously with receipt of at least a portion of the image by image digitization circuitry 120 forming a part thereof.

The combined, preferably simultaneously operative non-digitized and digitized imaging functionalities of instrument 100 render instrument 100 particularly useful to a user such as a medical professional, by allowing an image to be instantaneously and conveniently viewed by the user during examination via non-digitized viewing optics 128, whilst preferably simultaneously allowing the digital capture of the image for image processing, display, analysis and/or storage.

It is a further particular feature of a preferred embodiment of the present invention that instrument 100 and particularly optical examination and non-digitized viewing optics 128 thereof are configured such that the non-digitized image presented to a user is in focus on the user's eye, without requiring either manual or electronic focusing adjustments to be made to optical examination and non-digitized viewing optics 128. Head portion 104 and particularly optical examination and non-digitized viewing optics 128 therein therefore need not comprise adjustable focusing elements or focusing mechanisms associated therewith, thus advantageously simplifying the structure, complexity and cost of optics 128.

Additionally and simultaneously, optical examination and non-digitized viewing optics 128 are preferably arranged with respect to image digitization, storage and transmission circuitry 120 such that the image received by image digitization, storage and transmission circuitry 120 from optics 128 is in focus, without requiring either manual or electronic focusing adjustments to be made thereto. This is in contrast to conventional digital optical diagnostic tools, in which the image received at a digital sensor typically requires further focusing, either manually by a user or via an automatic mechanism.

Head portion 104 and hand-holdable portion 102 may be formed as modular components of instrument 100, such that hand-holdable portion 102 may be compatible for use with a variety of types of replaceable, removable optical examination head portions 104 of the present invention. In an alternative possible embodiment of the present invention, hand-holdable portion 102 may be configured so as to be capable of supporting more than one type of optical examination head portion 104 simultaneously thereupon. Alternatively, hand-holdable portion 102 may be a dedicated handle portion adapted for use with a single type of optical examination head portion 104 and optionally unitarily formed therewith.

Figure 2:
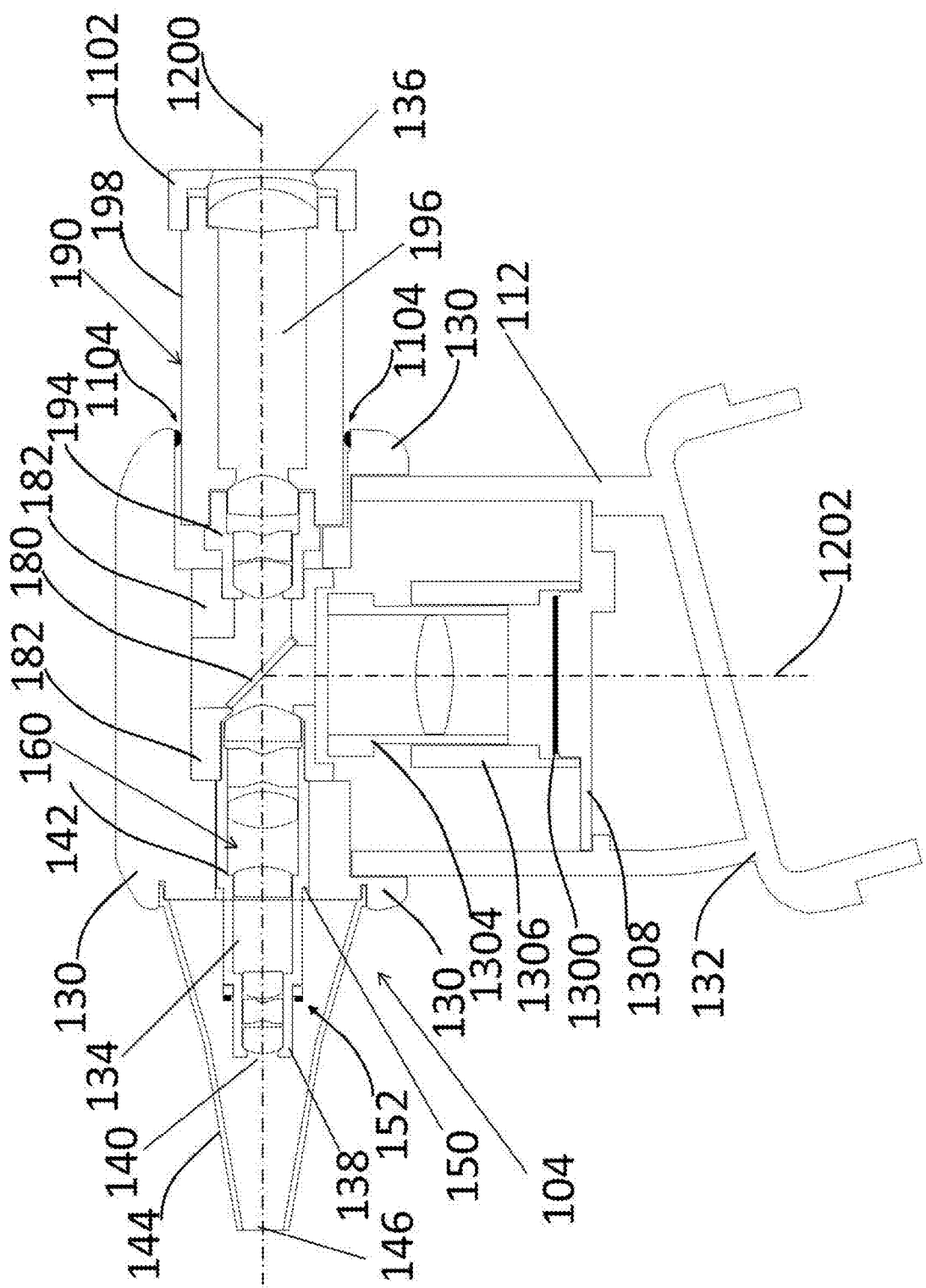

The operation of instrument 100 and particularly the manner in which instrument 100 performs dual, preferably at least partially simultaneous non-digitized and digitized imaging may be best understood with reference to FIGS. 2 and 3, showing simplified enlarged cross-sectional view illustrations of respective portions of a medical optical examination instrument of the type shown in FIGS. 1A and 1B.

As seen in FIG. 2, showing an enlarged cross-sectional view of optical examination head portion 104 mounted on neck portion 112, head portion 104 is here embodied as an otoscope head portion. Components of otoscope head portion 104 are preferably housed by a main otoscope holder 130, which main otoscope holder 130 is preferably mounted on a neck housing 132 of neck portion 112. An elongate optical passage 134 is preferably formed along and within holder 130, which optical passage 134 preferably extends beyond the outer edges of holder 130 on either side thereof.

Optical passage 134 preferably has a first proximal end 136 positioned proximal to a user's eye when instrument 100 is in use and a second distal end 138 positioned proximal to the ear during examination thereof. Distal end 138 preferably comprises an opening 140 defined by a front end holder 142. Opening 140 is preferably enclosed by a distal insertion portion 144 insertable into the ear. Distal insertion portion 144 maybe embodied as a tip element 144 such as a speculum having a distal opening 146 aligned with opening 140.

Speculum 144 may be a disposable element removably attached to main holder 130. Alternatively, speculum 144 may be a reusable element integrally formed with optical passage 134. Speculum 144 is preferably adapted for insertion in the ear of a patient during examination thereof, as is well known in the art. Head portion 104 may optionally additionally include an insufflator port (not shown) into which air may be blown in order to apply pressure to the ear drum, as is well known in the art.

Otoscope front end holder 142 may be formed as a generally tubular element having staggered walls 150, a terminus of which defines opening 140. Otoscope front end holder 142 may include light sources for illuminating the field of view of the user during examination. Here, by way of example, a plurality of light sources 152 is shown to be located on an anterior portion of front end holder 142. Light sources 152 may be embodied as LEDs, emitting light of one or more wavelengths suitable for illumination of the field of view of instrument 100. By way of example only, LEDs 152 may emit UV and/or blue light.

An array of optical elements 160 is preferably housed by otoscope front end holder 142, the staggered walls 150 of which permit the housing of optical elements having varying heights. Array of optical elements 160 is preferably but not necessarily linear. With additional reference to FIG. 3, generally corresponding to FIG. 2 but with speculum 144 and an upper part of holder 130 removed for clarity of presentation, array optical elements 160 preferably includes a first train of lenses 162, a second lens 164 spaced apart from first train of lenses 162 and optically aligned therewith and a third train of lenses 166, spaced apart from second lens 164 and optically aligned therewith.

Head portion 104 further preferably includes a beam splitter 180, preferably located posterior to array of optical elements 160 and optically aligned therewith. Beam splitter 180 may be secured in place by a beam splitter holder 182 located adjacent to and abutting otoscope front end holder 142.

An eye piece 190 is preferably provided behind beam splitter 180 at proximal end 136. Eye piece 190 may comprise an anterior lens arrangement 192 preferably housed by a front eye piece holder 194 and located adjacent to beam splitter 180, a hollow channel 196 preferably defined by a central eye piece holder 198 and a posterior lens arrangement 1100 terminating at proximal end 136 and preferably held by an eye piece back cover 1102. Eye piece 190 is preferably aligned with main holder 130 and other elements of optical passage 134 by way of an aligning mechanism, such as an eye piece aligner 1104. Eye piece aligner 1104 preferably comprises a mechanical assembly for providing alignment adjustment of the optical components posterior to beam splitter 180.

It is appreciated that in this embodiment of instrument 100 optical passage 134 of head portion 104 may be composed of several sub-segments including a front end housed by front end holder 142, a central region enclosing beam splitter 180 housed by beam splitter holder 182 and an eye piece 190 housed by eye piece holder 198. It is understood, however, that this particular embodiment of optical passage 134 is illustrative and exemplary only and that head portion 104 may comprise any optical pathway therethrough having a variety of suitable configurations as are well known in the art, further examples of which are provided henceforth.

It is further appreciated that array of optical elements 160, beam splitter 180, anterior lens arrangement 192 and posterior lens arrangement 1100 of optical passage 134 comprise a preferred embodiment of optical examination and non-digitized viewing optics 128 of optical head portion 104. As understood from consideration of FIGS. 2 and 3, array of optical elements 160, beam splitter 180, anterior lens arrangement 192 and posterior lens arrangement 1100 are preferably aligned along a first common optical pathway 1200. First optical pathway 1200 is preferably but not necessarily a linear pathway, as illustrated herein. Depending on the design requirements of instrument 100, first optical pathway 1200 may be a curved pathway, in which case array of optical elements 160 may be non-linear and optical examination and non-digitized viewing optics 128 may include additional and/or alternative optical elements for deflecting the direction of light passing therethrough.

In operation of head portion 104, speculum 144 is preferably inserted in the ear of a patient to be examined, illumination of which is provided by LEDs 152. As best appreciated from consideration of FIG. 3, light reflected or scattered from the tympanic membrane of the ear of a patient enters head portion 104 through opening 140 and propagates towards first train of lenses 162. Opening 140 thus preferably forms the aperture stop of optics 128. First train of lenses 162 preferably comprises three optical elements, as shown herein, operative to form an image of the tympanic membrane. The image formed by first train of lenses 162 may be formed at a finite distance, such as at a first plane A, as shown in FIG. 3. Alternatively, first train of lenses 162 may be arranged so as to form an image at an infinite distance.

Second lens 164 is preferably a field lens, placed near the image formed at first plane A in order to relay an image of the aperture stop formed by opening 140 to the entrance pupil of image digitization, storage and transmission circuitry 120. Additionally, second lens 164 relays an image of the aperture stop formed by opening 140 to a location adjacent to third train of lenses 166. It is appreciated that although second lens 164 is shown herein to comprise a single optical element, second lens 164 may be modified to include a greater number of optical elements, depending on the optical requirements thereof.

Third train of lenses 166 is preferably operative to collimate light travelling therethrough. This is advantageous since should converging rather than collimated light pass through beam splitter 180, the converging light would acquire aberrations, thereby reducing the sharpness of the image. Additionally, collimation of light by third train of lenses 166 facilitates the use of a commercially available camera lens as part of image digitization, storage and transmission circuitry 120. It is appreciated that should beam splitter 180 be made very thin, such that aberrations produced thereby would be minimized, and/or should the use of a commercially available camera lens be avoided, third train of lenses 166 may be obviated since the collimating functionality thereof would be rendered unnecessary.

Anterior lens arrangement 192 is preferably operative to receive collimated light from third train of lenses 166 and produce an image at a finite distance therefrom, preferably between anterior lens arrangement 192 and posterior lens arrangement 1100 at a second plane B. Optics 128 thus preferably produce an even number of internal images, two in this case, at first plane A and second plane B. As a result, the view presented to a user viewing the image through posterior lens arrangement 1100 is upright. Should optics 128 produce an odd number of internal images, the view presented to a user viewing the image through posterior lens arrangement 1100 would be inverted.

Posterior lens arrangement 1100 functions as the eyepiece of head portion 104, producing an image of the tympanic membrane substantially at infinity, such that the image may be easily observed, thereby reducing the eye strain for users of instrument 100. Posterior lens arrangement 1100 is additionally preferably operative to form an exit pupil in the vicinity of the pupil of the user's eye, such as at a third plane C. The exit pupil may be at least 15 mm from posterior lens arrangement 1100 and preferably is at least 20 mm therefrom.

In use of instrument 100, a user may insert speculum 144 into the ear of a patient and look through proximal end 136 to see a non-digitized image of the inner ear. The user may make slight adjustments to the location of the instrument in the ear in order for the desired features of the inner ear to be in focus on the user's eye. It is understood that once instrument 100 is placed by the user in the desired location, an in-focus analogue image is preferably presented to the user, without requiring focusing adjustments to be made to the optical elements of optics 128. Optical elements 162, 164, 166, 180, 192 and 1100 thus preferably do not comprise adjustable optical elements and instrument 100, and particularly head portion 104 thereof, preferably does not include any manual or electronic focusing mechanisms.

Light impinging on beam splitter 180 from third train of lenses 166 is preferably split in two directions by beam splitter 180. A first portion of the light is preferably transmitted through beam splitter 180 and continues to travel through optical passage 134 along optical pathway 1200. A second portion of the light is reflected by beam splitter 180 in a direction that is angled with respect to first optical pathway 1200, so as to exit optical passage 134. Here, by way of example, the second portion of light is seen to be deflected along a second optical pathway 1202 in a direction generally perpendicular to first optical pathway 1200. Second optical pathway 1202 is preferably but not necessarily a linear pathway, as illustrated herein. Depending on the design requirements of instrument 100, second optical pathway 1202 may be a curved pathway, in which case optical examination and non-digitized viewing optics 128 may include additional and/or alternative optical elements for deflecting the direction of light passing therethrough, as is exemplified henceforth with reference to FIG. 14.

The first portion of light transmitted through beam splitter 180 along first optical pathway 1200 is preferably received by posterior and anterior lens arrangements 192, 1100 and forms a non-digitized image viewable by the user, as described above. It is appreciated that first optical pathway 1200 therefore constitutes a non-digital optical pathway, wherealong light emanating from the target is transmitted to a user, allowing the user to view a non-digitized image of the target.

Due at least to the unique arrangement of optical elements 162, 164, 166, 180, 192 and 1100 along first optical pathway 1200, the non-digitized image generated thereby is in focus on the user's eye when viewed by the user through eye piece 190, The user may thus immediately interpret the non-digitized image without any additional focusing adjustments to optics 128 in order to focus the image being required.

The second portion of light reflected by beam splitter 180 along second optical pathway 1202 is preferably incident upon image digitization circuitry 122, preferably comprising a digital sensor 1300. It is appreciated that second optical pathway 1202 thus constitutes a digital optical pathway, wherealong light emanating from the target is transmitted to digital sensor 1300, thus facilitating the formation of a digitized image of the target.

Digital sensor 1300 is preferably located in hand-holdable portion 102 and particularly preferably located in neck portion 112 thereof. It is appreciated, however, that digital sensor 1300 may alternatively be located in head portion 104. By way of example, head portion 104 may be formed including neck portion 112 therewith, whereby digital sensor 1300 located in neck portion 112 may be considered to constitute a part of head portion 104. It is understood that in the case that instrument 100 does not include neck portion 112, digital sensor 1300 may be located in alternative locations in handle 102 or head portion 104.

The second portion of light reflected by beam splitter 180 may be focused upon digital sensor 1300 by way of a lens system, here embodied by way of example as a single sensor lens 1302, which sensor lens 1302 is preferably aligned with second optical pathway 1202. The lens system relaying the second portion of light to digital sensor 1300 may alternatively comprise a group of lenses, as is detailed henceforth with reference to FIGS. 12-14.

It is appreciated that, due to the arrangement of optical elements 162, 164, 166 and 180 with respect to sensor lens 1302, the image received by digital sensor 1300 is in focus on digital sensor 1300, such that additional focusing adjustments in order to further focus the image are preferably largely or entirely unnecessary. The need for additional focusing elements and/or mechanisms associated with digital sensor 1300 is thus advantageously obviated.

It is understood that instrument 100 thus exhibits light propagation and image formation along two separate optical paths, namely a first non-digital optical path represented by first non-digital optical pathway 1200 and a second digital optical path represented by second digital optical pathway 1202, optical components along the first and second paths being arranged so as to produce respective focused analogue and digitized images. Advantageously, due to the generation of respective focused analogue and digitized images, at least one and preferably both of the non-digital and digital optical paths does not require the inclusion of adjustable focusing mechanisms or elements therein. Preferably, the in-focus analogue and digitized images are produced simultaneously.

Sensor lens 1302 may be secured by a sensor lens holder 1304 and housed in a sensor lens housing 1306. Digital sensor 1300 may be cooperatively coupled to a digital sensor board 1308. Digital sensor 1300 in combination with sensor lens 1302 and sensor board 1308 preferably comprises a digital camera for generating a digitized image of the target. The digitized image of the target may be a still image or may be a video frame forming a component of a digital video. Subsequent processing of the digital image or video produced at digital sensor 1300 is explained in greater detail below, with reference to FIGS. 4A and 4B.

It is appreciated that the particular above-described configuration of optical examination and non-digitized viewing optics 128 illustrated in FIGS. 1A-3 is exemplary only and that optical examination and non-digitized viewing optics 128 may be embodied as any arrangement of optical elements having optical examination and non-digitized viewing capabilities, capable of producing a focused analogue image on a user's eye, simultaneously with transmitting at least a portion of that image to image digitization circuitry so as to generate an in-focus digital image, preferably for transmission and/or storage.

Furthermore, although optical examination and non-digitized viewing optics 128 are described herein in the context of incorporation in instrument 100, optical examination and non-digitized viewing optics 128 are not limited to use in instrument 100 and may be incorporated in other types of digital and analogue otoscopes, with appropriate modifications as may be required. Additionally, it is appreciated that the particular above-described configuration of digital sensor 1300 is exemplary only and that digital sensor 1300 may be embodied as any digital camera having image digitization functionality.

Particularly, it is understood beam splitter 180 may comprise any optical device capable of splitting light emanating from the examined target so as to be directed along two separate optical pathways. By way of example, beam splitter 180 may comprise one or more stationary or mobile elements, such as moving mirrors or rotating elements. Furthermore, beam splitter 180 may split the light between first and second optical pathways 1200 and 1202 in any desired ratio, depending on the required intensity of the non-digitized and digitized images respectively.

Additionally, one or more components of head portion 104 shown herein may be replaced by alternative elements carrying out comparable or additional functions. By way of example, eye piece 190 may be augmented or replaced by a viewing screen to enhance the user's view of the non-digitized image.

It is appreciated that instrument 100, and particularly optics 128 thereof, are arranged to provide an in-focus analogue image to a user having standard vision. In this context, an in-focus analogue image is understood as an analogue image sufficiently in focus on the user's eye to allow performance of examination and/or diagnosis of the subject of the image by the user. In extreme cases, such as for example in the case of a user having very poor vision, head portion 104 may be adapted to include auto-focus technology or manual focus mechanisms, to aid a user in viewing the analogue image produced by optics 128.

Figure 4A:
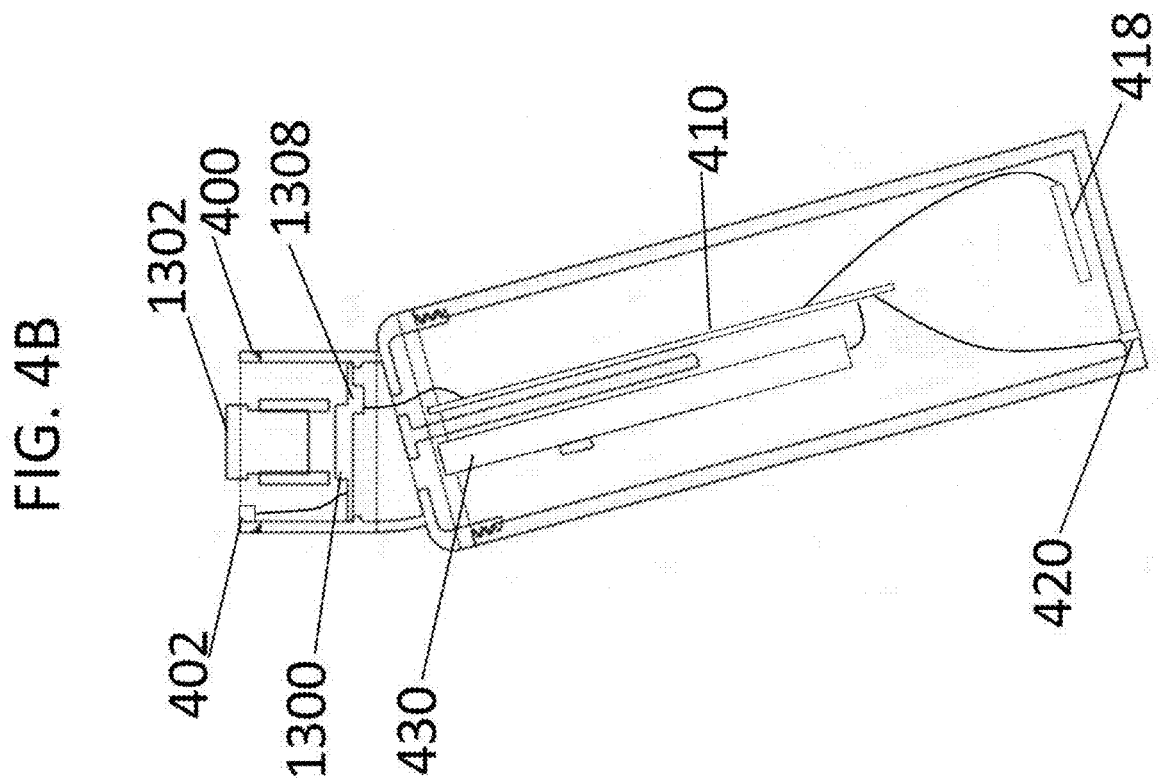
FIGS. 4A and 4B are simplified respective external perspective and cross-sectional view illustrations of a handle portion useful in a medical optical examination instrument of the present invention.
Figure 4B:
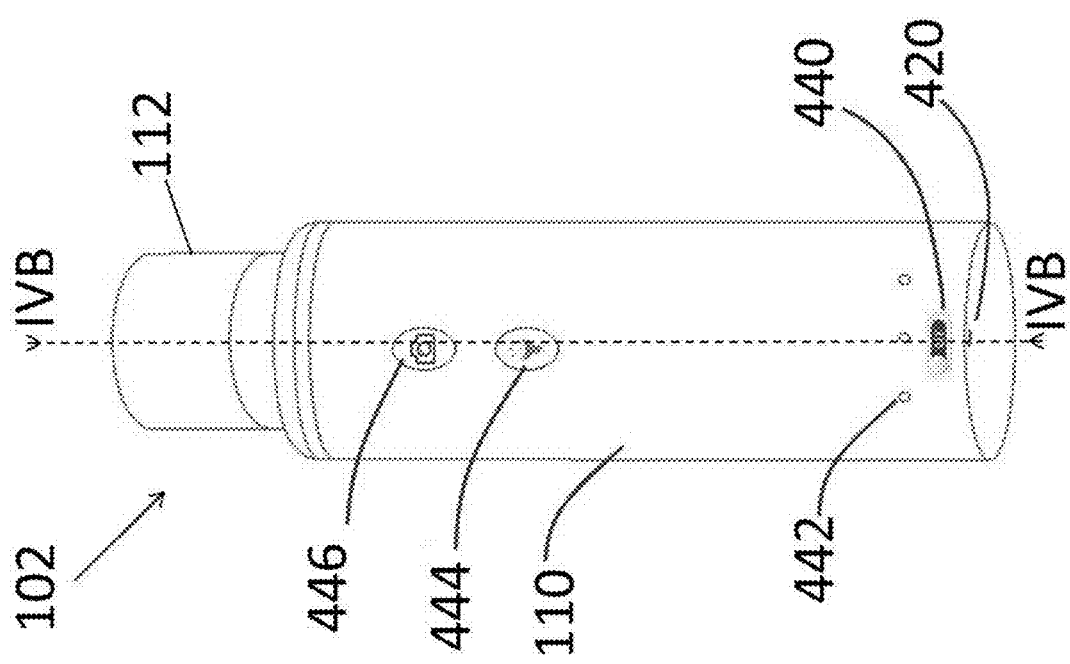

Reference is now made to FIGS. 4A and 4B, which are simplified respective external perspective and cross-sectional view illustrations of a handle portion useful in a medical optical examination instrument of the type show in FIGS. 1A-3.

As seen in FIGS. 4A and 4B, and as detailed above with reference to FIGS. 1A and 1B, hand-holdable portion 102 may include body portion 110 and neck portion 112, upon which neck portion 112 a head portion of the device of the present invention is preferably mountable. It is appreciated, however, that the delineation of body portion 110 and neck portion 112 is for ease of description only and that hand-holdable portion 102 may alternatively be formed as a continuous element, the neck of which is indistinguishable from the body. Alternatively, hand-holdable portion 102 may be unitarily formed with head portion 104 as a single element.

As described hereinabove with reference to FIGS. 2 and 3, hand-holdable portion 102 may include image digitization circuitry 122, here embodied as digital image sensor 1300 coupled to sensor board 1308, for digitizing an image received from optics 128 in head portion 104. Digital sensor 1300 in combination with sensor board 1308 may be operative to create individual digitized images and/or videos based on images received from non-digitized optics 128.

Here, by way of example, digital image sensor 1300 and sensor board 1308 are shown to be located in neck portion 112 proximate to head portion 104, although it is appreciated that digital image sensor 1300 and sensor board 1308 may be moved to alternative locations within hand-holdable portion 102. It is further appreciated that digital image sensor 1300 and sensor board 1308 may alternatively be located in head portion 104 of instrument 100.

Neck portion 112 may include a locking mechanism 400 for securing head portion thereon and for ensuring correct optical alignment of optics 128 with sensor 1300. An LED power connection 402 adapted for providing power to LEDs 152 may also be provided on an upper portion of neck 112.

Figure 5:
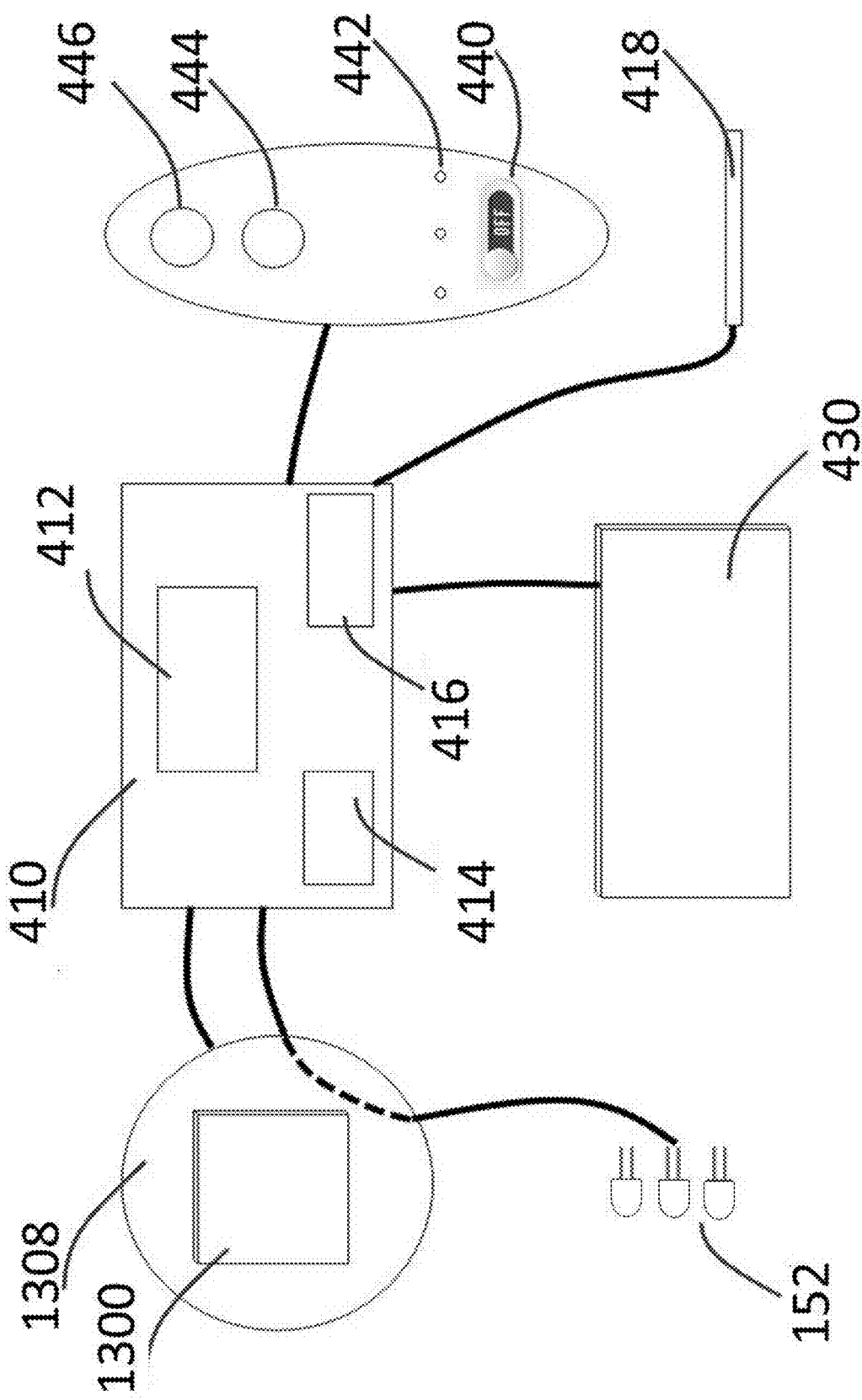
FIG. 5 is a simplified partially pictorial block diagram illustrating components useful in a handle portion of the type shown in FIGS. 4A and 4B.

Sensor board 1308 is preferably connected to a main controller board 410 located in handle body 110. Referring additionally to FIG. 5, main controller board 410 preferably includes a main controller module 412 for controlling the operation of instrument 100 including at least LEDs 152 and image digitization, storage and transmission circuitry 120. Main controller board 410 preferably additionally includes an internal embedded or removable memory and storage module 414 for storage of digitized images or videos created at digital sensor 1300 and a wireless connection module 416, such as a WiFi module. Wireless connection module 416 is preferably connected to at least one antenna, such as an antenna 418 located in handle portion 102 and operative to wirelessly transmit digitized images or videos to an external device, such as a PC. It is appreciated that handle portion 102 may alternatively include multiple antennas, depending on the transmission requirements thereof.

Additionally or alternatively to wireless transfer of digitized images or videos by way of at least one antenna 418, digitized images or videos generated by digital sensor 1300 may be wired to an external device. In order to facilitate wired transfer of data therefrom, handle portion 102 may include a connection port, such as a USB port 420.

It is understood that main controller board 410 and particularly memory and storage module 414 thereof constitutes a particularly preferred embodiment of image storage circuitry 124 and wireless connection module 416 and antenna 418 constitute particularly preferred embodiments of image transfer circuitry 126.

In accordance with a particularly preferred embodiment of the present invention, image digitization, storage and transmission circuitry 120 in at least one of handle portion 102 and head portion 104 is operative to perform live video streaming of digitized videos to the external computing device in real time. The videos of the target may be displayed on a screen of the external computing device effectively simultaneously with a user viewing the target in an analogue fashion through non-digitized optics 128 of instrument 100.

Instrument 100 may be powered by a battery 430, preferably located in handle portion 102 and connected at least to main controller board 410 and digital sensor board 1308. Battery 430 may be any type of battery suitable for providing power to instrument 100 and may be rechargable by way of one or more of a variety of mechanisms, including inductive charging, cradle or wired charging.

Handle portion 102 may optionally additionally include an image analysis module (not shown) for use in analyzing digitized images or videos generated by image digitization circuitry 122 in order to aid diagnosis based thereon. Alternatively, image analysis functionality may be included in an external device to which instrument 100 may be connected.

Instrument 100, and preferably body portion 110 thereof, may also include a plurality of user control features for operating and monitoring operation of instrument 100, including, by way of example only, an on/off control feature 440, a series of power, battery and connectivity indicators 442, an LED control button 444 and an image or video capture feature 446. Image or video capture feature 446 allows a user to initiate capture of digitized still images or digitized video frames by image digitization circuitry 122. Image or video capture feature 446 may be a press button as illustrated herein or may be any other type of control feature such as a trigger.

It is appreciated that one or more of the control features shown in FIGS. 4A and 5 may be obviated or replaced by other features performing equivalent functions. Thus, by way of example, LED control button 444 may be obviated and the operation of LEDs 152 instead controlled by a touch sensor located in handle portion 102.

Figure 6:
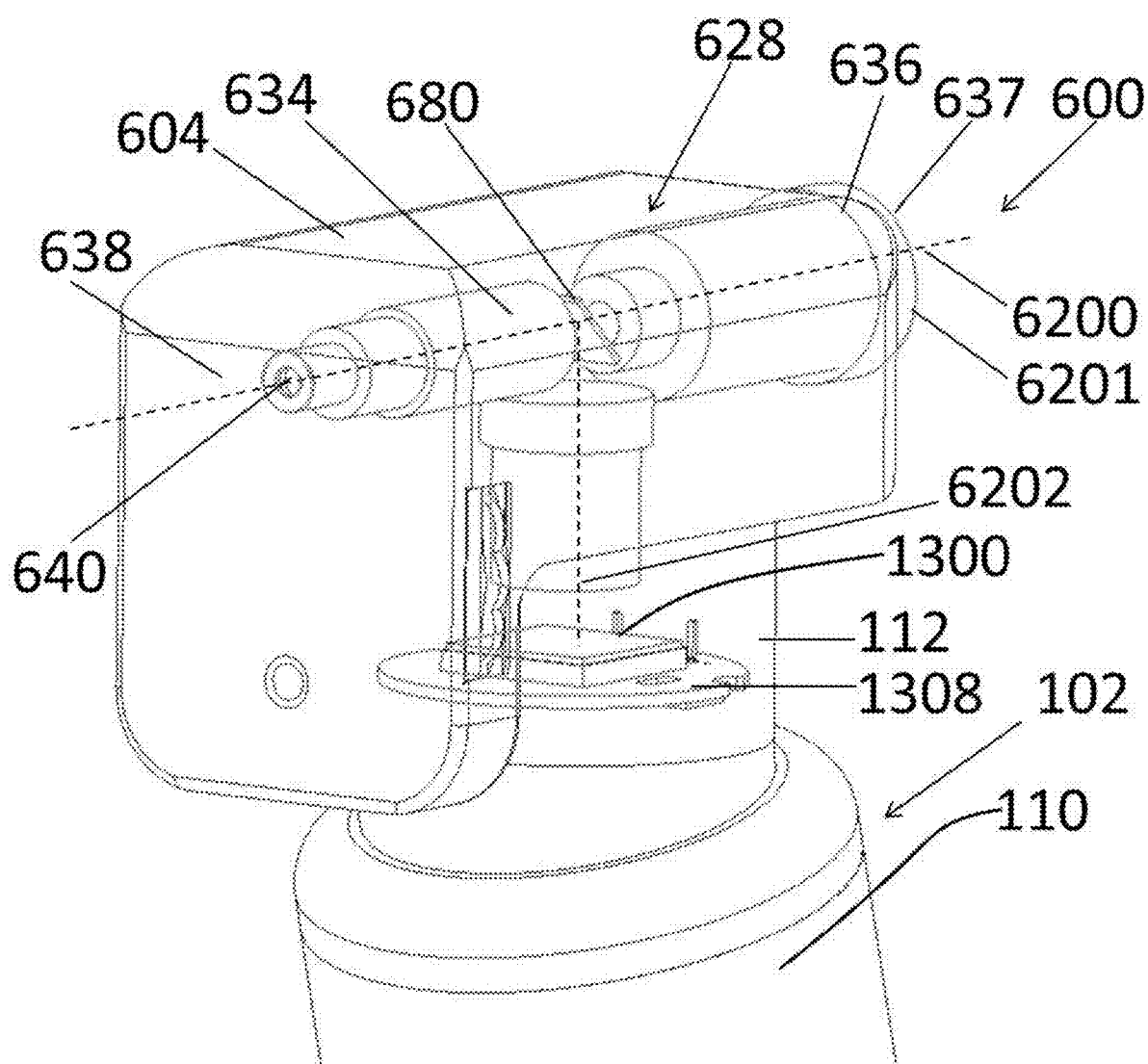
FIG. 6 is a simplified schematic perspective view illustration of a portion of a medical optical examination instrument, constructed and operative in accordance with another preferred embodiment of the present invention.
Figure 7:
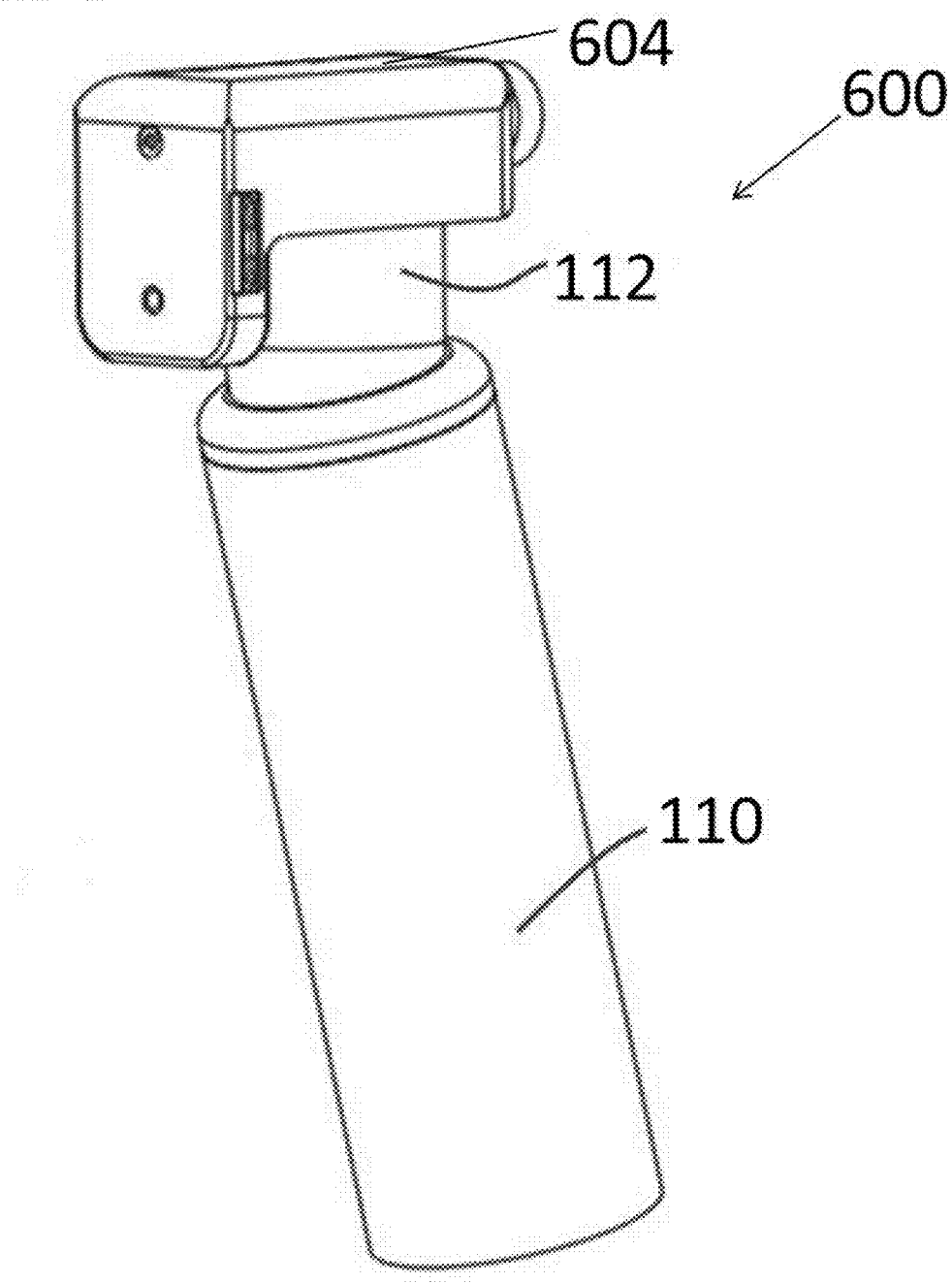
FIG. 7 is a simplified schematic assembled view illustration of a medical optical examination instrument of the type shown in FIG. 6 including a handle portion of the type shown in FIGS. 4A and 4B.

Reference is now made to FIG. 6, which is a simplified schematic perspective view illustration of a portion of a medical optical examination instrument, constructed and operative in accordance with another preferred embodiment of the present invention and to FIG. 7, which is a simplified schematic assembled view illustration of a medical optical examination instrument of the type shown in FIG. 6 including a handle portion of the type shown in FIGS. 4A and 4B.

As seen in FIGS. 6 and 7, there is provided a medical optical examination instrument 600, preferably including hand-holdable portion 102 forming a handle of instrument 600 and at least an optical examination head portion 604 mountable on hand-holdable portion 102. Here, by way of example only, optical examination head portion 604 is seen to be embodied as an ophthalmoscope head portion 604, such that medical optical examination instrument 600 functions as an ophthalmoscope.

As seen most clearly in FIG. 6, ophthalmoscope head portion 604 may include an optical passage 634 having a proximal end 636 defining a proximal opening 637 and a distal end 638 defining a distal opening 640. It is appreciated that instrument 600 is rendered partially transparent in FIG. 6 in order to more clearly depict the elements housed therein.

Proximal opening 637 is preferably adapted for positioning in proximity to a user's eye and distal opening 640 is preferably adapted for positioning in proximity to a target during examination thereof. Ophthalmoscope head portion 604 further preferably includes additional examination and functional features typical of ophthalmoscopes as are well known in the art.

Hand-holdable portion 102 is preferably of the type illustrated in FIGS. 4A-5 and preferably includes body portion 110 and neck portion 112, on which neck portion 112 head portion 604 is preferably mounted. Ophthalmoscope optical examination head portion 604 preferably includes at least optical examination and non-digitized viewing optics generally designated by a reference number 628. Optical examination and non-digitized viewing optics 628 are preferably operative to form an image of a target such as the fundus of an eye of a patient.

It is a particular feature of a preferred embodiment of the present invention that image digitization, storage and transmission circuitry 120 included in instrument 600 is arranged to receive an image from at least a portion of at least optical examination and non-digitized viewing optics 628 when head portion 604 is mounted on hand-holdable portion 102. Image digitization, storage and transmission circuitry 120 is preferably located in at least one of handle 102 and head portion 604 and here, by way of example, is entirely located in handle 102.

Receipt of an image from optics 628 in head portion 604 by image digitization, storage and transmission circuitry 120 preferably occurs at least partially simultaneously with the image being viewable by a user via optical examination and non-digitized viewing optics 628. It is appreciated that instrument 600 thus constitutes a multifunctional instrument, allowing a user to view an image captured thereby in a non-digitized, analogue fashion in addition to and preferably simultaneously with receipt of at least a portion of the image by image digitization circuitry 120 forming a part thereof.

It is a further particular feature of a preferred embodiment of the present invention that instrument 600 and particularly optical examination and non-digitized viewing optics 628 thereof are configured such that the non-digitized image presented to a user is in focus on the user's eye, without requiring either manual or electronic focusing adjustments to be made to optical examination and non-digitized viewing optics 128. The user may thus immediately interpret the non-digitized image without any additional focusing adjustments to the image being required. Instrument 600 and particularly optical examination and non-digitized viewing optics 628 thereof therefore need not comprise adjustable focusing elements or focusing mechanisms associated therewith, thus advantageously simplifying the structure, complexity and cost of optics 628.

Additionally and simultaneously, optical examination and non-digitized viewing optics 628 are preferably arranged with respect to image digitization, storage and transmission circuitry 120 such that the image received by image digitization, storage and transmission circuitry 120 from optics 628 is instantaneously in focus on digital sensor 1300, additional focusing of the image on digital sensor 1300 thereby being rendered largely or entirely unnecessary. The need for additional focusing elements and/or mechanisms associated with digital sensor 1300 is thus advantageously obviated. This is in contrast to conventional digital optical diagnostic tools, in which the image received at a digital sensor typically requires focusing, either manually by a user or via an automatic mechanism.

The combined, preferably simultaneously operative non-digitized and digitized imaging functionalities of instrument 600 render instrument 600 particularly useful to a user such as a medical professional, by allowing an image to be instantaneously and conveniently viewed by the user during examination via non-digitized viewing optics 628, whilst preferably simultaneously allowing the digital capture of the image for subsequent image processing, analysis and/or storage.

Ophthalmoscope head portion 604 and hand-holdable portion 102 may be formed as modular components of instrument 600, such that hand-holdable portion 102 may be compatible for use with a variety of types of replaceable, removable optical examination head portions of the present invention. Alternatively, hand-holdable portion 102 may be a dedicated handle portion adapted for use with ophthalmoscope head portion 604 and optionally unitarily formed therewith.

As seen most clearly in FIG. 6, non-digitized viewing optics 628 preferably includes a beam splitter 680. Light emanating from the target to be examined preferably enters instrument 600 via distal opening 640 and is preferably transmitted through optical passage 634 to beam splitter 680. A first portion of light impinging on beam splitter 680 is preferably transmitted therethrough along a first optical pathway 6200 to proximal opening 637, here preferably embodied as an eye piece 6201, whereat a user may view a non-digitized image of the examined region. The image of the examined target thus may be directly viewed by the user instantaneously upon examination of the target in a non-digitized, analogue fashion. It is appreciated that first optical pathway 6200 thus constitutes a non-digital optical pathway, wherealong light emanating from the target is transmitted to a user, thus allowing the user to view a non-digitized image of the target. First optical pathway 6200 may be linear, as illustrated herein, or non-linear.

A second portion of light impinging on beam splitter 680 is preferably reflected thereby along a second optical pathway 6202. The reflected light is preferably incident upon digital sensor 1300, preferably located in hand-holdable portion 102 and particularly preferably located in neck portion 112 thereof. It is appreciated that second optical pathway 6202 thus constitutes a digital optical pathway, wherealong light emanating from the target is transmitted to digital sensor 1300, thus facilitating the formation of a digitized image of the target. Second optical pathway 6202 may be linear, as illustrated herein, or non-linear.

It is understood that instrument 600 thus exhibits light propagation and image formation along two separate optical paths, namely a first non-digital optical path represented by first non-digital optical pathway 6200 and a second digital optical path represented by second digital optical pathway 6202, optical components along the first and second paths being arranged so as to produce respective focused analogue and digitized images. Advantageously, due to the generation of respective focused analogue and digitized images, at least one and preferably both of the non-digital and digital optical paths does not require the inclusion of adjustable focusing mechanisms or elements therein. Preferably, the in-focus analogue and digitized images are produced simultaneously.

Subsequent processing of the digitized image or video is generally as described above, with reference to FIGS. 4A-5.

It is appreciated that although digital sensor 1300 is here shown to be located in handle portion 102, digital sensor 1300 may alternatively be located in head portion 604. By way of example, head portion 604 may be formed including neck portion 112 therewith, whereby digital sensor 1300 located in neck portion 112 may be considered to constitute a part of head portion 604. It is understood that in the case that instrument 600 does not include neck portion 112, digital sensor 1300 may be located in alternative locations in handle 102 or head portion 604.

It is understood that instrument 600 thus may generally resemble instrument 100 in relevant functional and design aspects thereof, with the exception of instrument 600 including an ophthalmoscope head portion 604, in contrast to the otoscope head portion 104 included in instrument 100.

Figure 8:
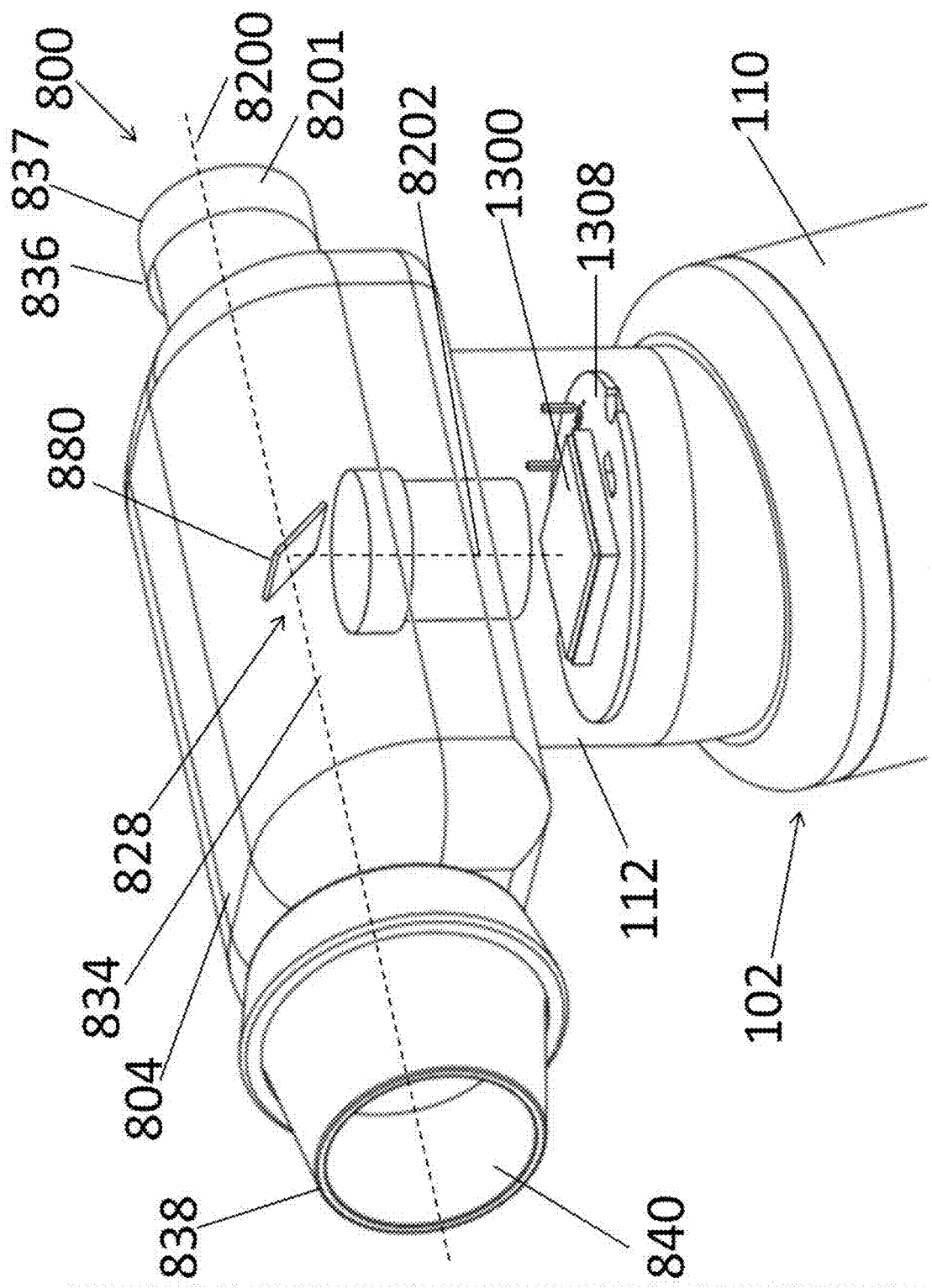
FIG. 8 is a simplified schematic perspective view illustration of a portion of medical optical examination instrument, constructed and operative in accordance with a further preferred embodiment of the present invention.
Figure 9:
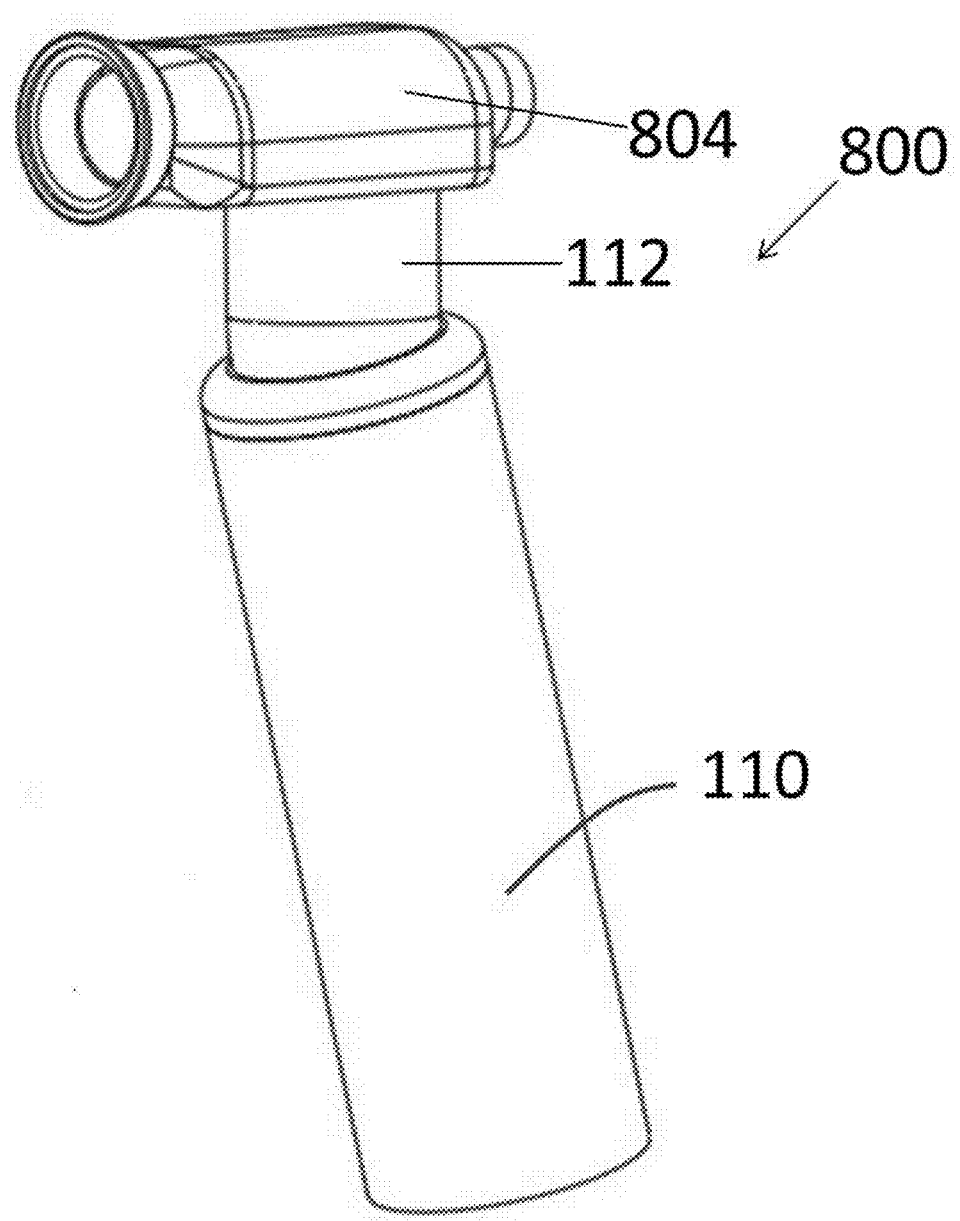
FIG. 9 is a simplified schematic assembled view illustration of a medical optical examination instrument of the type shown in FIG. 8 including a handle portion of the type shown in FIGS. 4A and 4B.

Reference is now made to FIG. 8, which is a simplified schematic perspective view illustration of a portion of a medical optical examination instrument, constructed and operative in accordance with another preferred embodiment of the present invention and to FIG. 9, which is a simplified schematic assembled view illustration of a medical optical examination instrument of the type shown in FIG. 8 including a handle portion of the type shown in FIGS. 4A and 4B.

As shown in FIGS. 8 and 9, there is provided a medical optical examination instrument 800, preferably including hand-holdable portion 102 forming a handle of instrument 800 and at least an optical examination head portion 804 mountable on hand-holdable portion 102. Here, by way of example only, optical examination head portion 804 is seen to be embodied as a dermatoscope head portion 804, such that medical optical examination instrument 800 functions as a dermatoscope. Dermatoscope head portion 804 may include an optical passage 834 having a proximal end 836 defining a proximal opening 837 and a distal end 838 defining a distal opening 840. Proximal opening 837 is preferably adapted for positioning in proximity to a user's eye and distal opening 840 is preferably adapted for positioning in proximity to a target during examination thereof. Dermatoscope head portion 804 further preferably includes examination and functional features typical of dermatoscopes as are well known in the art. It is appreciated that instrument 800 is rendered partially transparent in FIG. 8 in order to more clearly depict the elements housed therein.

Hand-holdable portion 102 is preferably of the type illustrated in FIGS. 4A-5 and preferably includes body portion 110 and neck portion 112, on which neck portion 112 head portion 804 is preferably mounted. Dermatoscope optical examination head portion 804 preferably includes at least optical examination and non-digitized viewing optics generally designated by a reference number 828. Optical examination and non-digitized viewing optics 828 are preferably operative to form an image of a target such as the skin of a patient.

It is a particular feature of a preferred embodiment of the present invention that image digitization, storage and transmission circuitry 120 included in instrument 800 is arranged to receive an image from at least a portion of at least optical examination and non-digitized viewing optics 828 when head portion 804 is mounted on hand-holdable portion 102. Image digitization, storage and transmission circuitry 120 is preferably located in at least one of handle 102 and head portion 804 and here, by way of example, is entirely located in handle 102.

Receipt of an image from optics 828 in head portion 804 by image digitization, storage and transmission circuitry 120 preferably occurs at least partially simultaneously with the image being viewable by a user via optical examination and non-digitized viewing optics 828. It is appreciated that instrument 800 thus constitutes a multifunctional instrument, allowing a user to view an image captured thereby in a non-digitized, analogue fashion in addition to and preferably simultaneously with receipt of at least a portion of the image by image digitization circuitry 120 forming a part thereof.

It is a particular feature of a preferred embodiment of the present invention that instrument 800 and particularly optical examination and non-digitized viewing optics 828 are preferably configured such that the non-digitized image presented to a user is in focus on the user's eye when viewed by the user, without requiring either manual or electronic focusing adjustments to be made to optical examination and non-digitized viewing optics 828. The user may thus immediately interpret the non-digitized image without any additional focusing adjustments to the image being required. Optical examination and non-digitized viewing optics 828 therefore need not comprise adjustable focusing elements or focusing mechanisms associated therewith, thus advantageously simplifying the structure, complexity and cost of optics 828.

Additionally and simultaneously, optical examination and non-digitized viewing optics 828 are preferably arranged with respect to image digitization, storage and transmission circuitry 120 such that the image received by image digitization, storage and transmission circuitry 120 from optics 828 is instantaneously in focus on digital sensor 1300, additional focusing of the image on digital sensor 1300 thereby being rendered largely or entirely unnecessary. The need for additional focusing elements and/or mechanisms associated with digital sensor 1300 is thus advantageously obviated. This is in contrast to conventional digital optical diagnostic tools, in which the image received at a digital sensor typically requires focusing, either manually by a user or via an automatic mechanism.

The combined, preferably simultaneously operative non-digitized and digitized imaging functionalities of instrument 800 render instrument 800 particularly useful to a user such as a medical professional, by allowing an image to be instantaneously and conveniently viewed by the user during examination via non-digitized viewing optics 828, whilst preferably simultaneously allowing the digital capture of the image for subsequent image processing, analysis and/or storage.

Dermatoscope head portion 804 and hand-holdable portion 102 may be formed as modular components of instrument 800, such that hand-holdable portion 102 may be compatible for use with a variety of types of replaceable, removable optical examination head portions of the present invention. Alternatively, hand-holdable portion 102 may be a dedicated handle portion adapted for use with dermatoscope head portion 804 and optionally unitarily formed therewith.

As seen most clearly in FIG. 8, non-digitized viewing optics 828 preferably include a beam splitter 880. Light received from the target to be examined preferably enters instrument 800 via distal opening 840 and is preferably transmitted along optical passage 834 to beam splitter 880. A first portion of light impinging on beam splitter 880 is preferably transmitted therethrough along a first optical pathway 8200 to proximal opening 837, which proximal opening 837 preferably comprises an eye piece 8201, whereat a user may view a non-digitized image of the examined region. The image of the examined target thus may be directly viewed by the user instantaneously upon examination of the target in a non-digitized, analogue fashion. It is appreciated that first optical pathway 8200 thus constitutes a non-digitized optical pathway, wherealong light emanating from the target is transmitted to a user, thus allowing the user to view a non-digitized image of the target. First optical pathway 8200 may be linear, as illustrated herein, or non-linear.

A second portion of light impinging on beam splitter 880 is preferably reflected thereby along a second optical pathway 8202. The reflected light is preferably incident upon digital sensor 1300, preferably located in hand-holdable portion 102 and particularly preferably located in neck portion 112 thereof. It is appreciated that second optical pathway 8202 thus constitutes a digital optical pathway, wherealong light emanating from the target is transmitted to digital sensor 1300, thus facilitating the formation of a digitized image or video of the target. Second optical pathway 8202 may be linear, as illustrated herein, or non-linear.

It is understood that instrument 800 thus exhibits light propagation and image formation along two separate optical paths, namely a first non-digital optical path represented by first non-digital optical pathway 8200 and a second digital optical path represented by second digital optical pathway 8202, optical components along the first and second paths being arranged so as to produce respective focused analogue and digitized images. Advantageously, due to the generation of respective focused analogue and digitized images, at least one and preferably both of the non-digital and digital optical paths does not require the inclusion of adjustable focusing mechanisms or elements therein. Preferably, the in-focus analogue and digitized images are produced simultaneously.

Subsequent processing of the digitized image or video is generally as described above, with reference to FIGS. 4A-5.

It is appreciated that although digital sensor 1300 is here shown to be located in handle portion 102, digital sensor 1300 may alternatively be located in head portion 804. By way of example, head portion 804 may be formed including neck portion 112 therewith, whereby digital sensor 1300 located in neck portion 112 may be considered to constitute a part of head portion 804. It is understood that in the case that instrument 800 does not include neck portion 112, digital sensor 1300 may be located in alternative locations in handle 102 or head portion 804.

It is understood that instrument 800 thus may generally resemble instruments 100 and 600 in relevant functional and design aspects thereof, with the exception of instrument 800 including a dermatoscope head portion 804, in contrast to the otoscope and opthalmoscope head portions 104 and 604 included in instruments 100 and 600, respectively.

Figure 10:
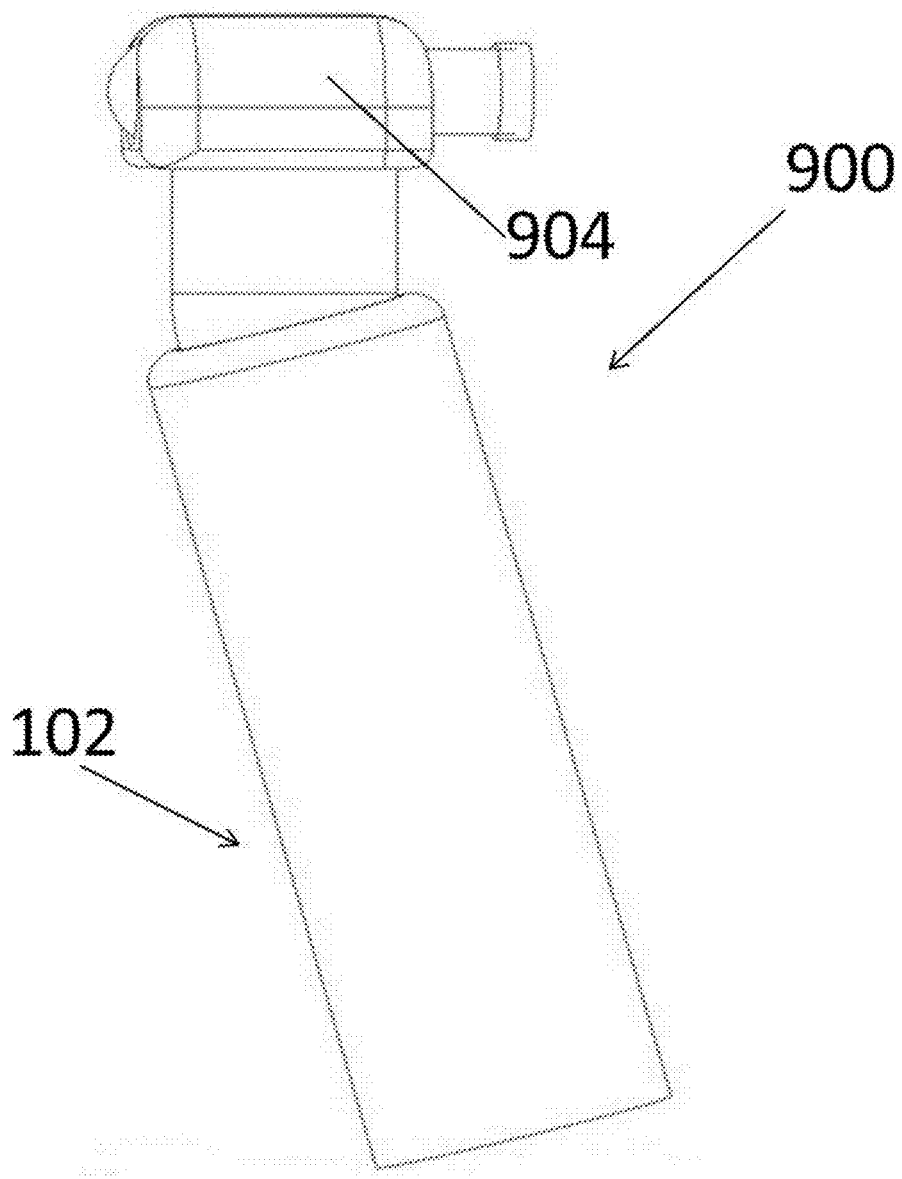
FIG. 10 is a simplified schematic assembled view illustration of a medical optical examination instrument constructed and operative in accordance with still another preferred embodiment of the present invention, including a handle portion of the type shown in FIGS. 4A and 4B.

It is appreciated that the optical examination head portion of the present invention is not limited to being embodied as otoscope head portion 104, ophthalmoscope head portion 604 or dermatoscope head portion 804, but rather may be embodied as any suitable optical examination head portion. Thus, as illustrated in the case of an instrument 900 shown in FIG. 10, head portion 104 may be formed as a general purpose examination head portion 904 mountable on handle 102. General purpose examination head portion 904 may be used to optically examine wider areas of the body, such as wounds, scars or nails, and may generally resemble head portions 104, 604 and 804 in all relevant aspects thereof.

Figure 11:
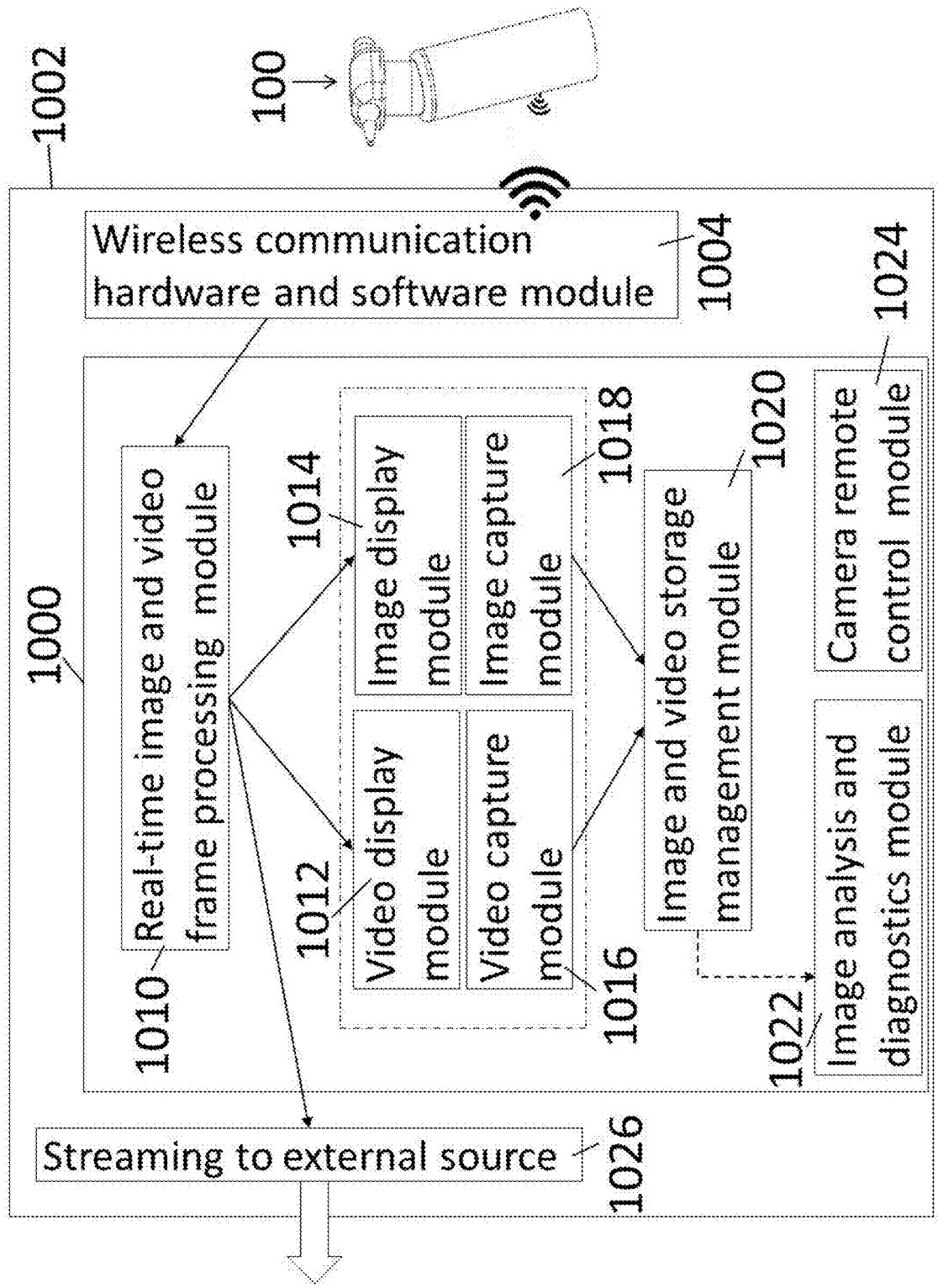
FIG. 11 is a simplified block diagram illustrating image processing functionalities useful in conjunction with a medical optical examination instrument of the present invention.

Reference is now made to FIG. 11, which is a simplified block diagram illustrating image processing functionalities useful in conjunction with a medical optical examination instrument of the present invention.

As seen in FIG. 11, a set of modular image processing and management functionalities 1000, useful in conjunction with any one of instruments 100, 600, 800 or 900 may be provided. Modular image processing and management functionalities 1000 may be carried out by an external computing device to which an instrument of the present invention may be connected by a wired or wireless connection. Such an external computing device preferably includes a non-transitory computer readable medium having stored thereupon computer instructions including code segments having image processing and management functionalities 1000.

Here, by way of example, instrument 100 is shown to be wirelessly connected to an external computing device generally represented by reference number 1002. External computing device 1002 preferably includes a wireless communication hardware and/or software module 1004 for facilitating wireless communication of computing device 1002 with instrument 100. External computing device 1002 may be any computing device such as a tablet, PC or smartphone.

Image processing and management functionalities 1000 may include a real-time video and/or image processing module 1010 communicatively coupled to at least one of a video display module 1012 and an image display module 1014. Videos and images displayed at video display module 1012 and image display module 1014 respectively may be captured by a video capture module 1016 and an image capture module 1018 respectively. The videos and/or images so captured may then be transferred to an image video storage and management module 1020, operative to store, organize and generally manage the videos and/or images. Video storage and management module 1020 may optionally be connected to an image analysis module 1022, as shown herein. Alternatively, as detailed above with reference to FIGS. 4A and 4B, image analysis module 1022 may be included as a functional module housed in handle portion 102 rather than in a computing device external thereto.

Image processing and management functionalities 1000 may additionally include a camera remote control module 1024, for remote control of digital sensor 1300 and sensor board 1308. Camera remote control module 1024 may be connected to image and video display and capture modules 1010-1018, such that sensor settings may be adjusted responsive to captured image and/or video quality parameters.

Computing device 1002 may further include a streaming module 1026 connected to real-time video and/or image processing module 1010, for streaming of data to an external source such as a telemedicine system.

Figure 12:
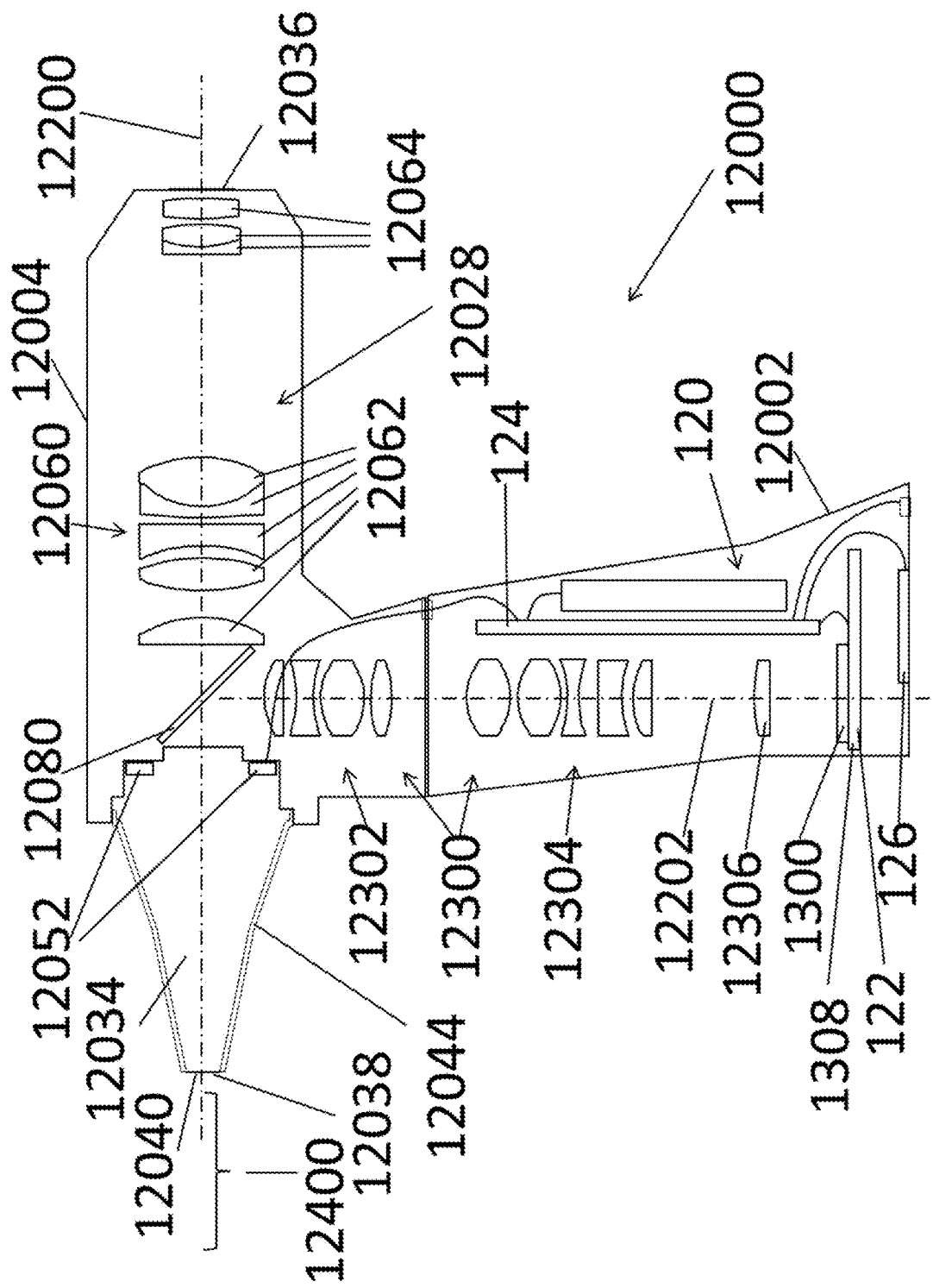
FIG. 12 is a simplified cross-sectional view illustration of a medical optical examination instrument constructed and operative in accordance with yet a further preferred embodiment of the present invention.

Reference is now made to FIG. 12, which is a simplified cross-sectional view illustration of a medical optical examination instrument constructed and operative in accordance with yet a further preferred embodiment of the present invention.

As seen in FIG. 12, there is provided a medical optical examination instrument 12000, preferably including a hand-holdable portion 12002 forming a handle of instrument 12000 and at least an optical examination head portion 12004 mountable on hand-holdable portion 12002. Here, by way of example only, optical examination head portion 12004 is seen to be embodied as an otoscope head portion 12004, such that medical optical examination instrument 12000 functions as an otoscope. It is appreciated, however, that optical examination head portion 12004 is not limited to being an otoscope head portion and that medical optical examination instrument 12000 is correspondingly not limited to functioning as an otoscope. Rather, instrument 12000 may be embodied as one of a variety of types of medical optical examination instruments, including an ophthalmoscope, dermatoscope or general purpose optical examination tool, with appropriate modifications as are well known in the art.

Instrument 12000 preferably includes image digitization, storage and transmission circuitry, generally designated by reference number 120. Image digitization, storage and transmission circuitry 120 is preferably included in at least one of hand-holdable portion 12002 and optical examination head portion 12004. Here, by way of example, image digitization, storage and transmission circuitry 120 is shown to be entirely located in hand-holdable portion 12002. It is appreciated, however, that image digitization, storage and transmission circuitry 120 may alternatively be entirely located in head portion 12004 or distributed between hand-holdable portion 12002 and head portion 12004 depending on the design requirements of the optical examination instrument of the present invention.

Image digitization, storage and transmission circuitry 120 may comprise image digitization component 122, image storage component 124 and image transmission component 126, by way of example. Further details concerning the structure and operation of image digitization, storage and transmission circuitry 120 are as provided with reference to FIGS. 4A, 4B, 5 and 11.

Instrument 12000 further preferably includes at least optical examination and non-digitized viewing optics generally designated by a reference number 12028. Optical examination and non-digitized viewing optics 12028 are preferably included in optical examination head portion 12004. Optical examination and non-digitized viewing optics 12028 are preferably operative to provide an image of a target. Preferably, optical examination and non-digitized viewing optics 12028 are operative to form a non-digitized image of a target such as the ear canal and tympanic membrane of a patient, in the case that optical examination head portion 12004 comprises an otoscope head portion.

It is a particular feature of a preferred embodiment of the present invention that image digitization, storage and transmission circuitry 120 is arranged to receive an image from at least a portion of at least optical examination and non-digitized viewing optics 12028, preferably when head portion 12004 is mounted on hand-holdable portion 12002.

Receipt of an image from optics 12028 in head portion 12004 by image digitization, storage and transmission circuitry 120 preferably occurs at least partially simultaneously with the image being viewable by a user via optical examination and non-digitized viewing optics 12028. It is appreciated that instrument 12000 thus constitutes a multifunctional instrument, allowing a user to view an image captured thereby in a non-digitized, analogue fashion in addition to and preferably simultaneously with receipt of at least a portion of the image by image digitization circuitry 120 forming a part thereof.

The combined, preferably simultaneously operative non-digitized and digitized imaging functionalities of instrument 12000 render instrument 12000 particularly useful to a user such as a medical professional, by allowing an image to be instantaneously and conveniently viewed by the user during examination via non-digitized viewing optics 12028, whilst preferably simultaneously allowing the digital capture of the image for image processing, display, analysis and/or storage.

As is detailed herein with reference to FIGS. 4A, 4B, 5 and 11, image digitization, storage and transmission circuitry 120 may be operative to digitize, store and transfer individual digitized images. Additionally or alternatively, image digitization, storage and transmission circuitry 120 may be operative to digitize, store and transfer digitized videos, including performing live video streaming of such digitized videos to an external computing device in real time.

It is a further particular feature of a preferred embodiment of the present invention that instrument 12000 and particularly optical examination and non-digitized viewing optics 12028 thereof are configured such that the non-digitized image presented to a user is in focus on the user's eye, without requiring either manual or electronic focusing adjustments to be made to the image, and particularly to optical examination and non-digitized viewing optics 12028. Head portion 12004 and particularly optical examination and non-digitized viewing optics 12028 therein therefore need not comprise adjustable focusing elements or focusing mechanisms associated therewith, thus advantageously simplifying the structure, complexity and cost of optics 12028.

Additionally and simultaneously, optical examination and non-digitized viewing optics 12028 are preferably arranged with respect to image digitization, storage and transmission circuitry 120 such that the image received by image digitization, storage and transmission circuitry 120 from optics 12028 is in focus, without requiring either manual or electronic focusing adjustments to be made thereto. This is in contrast to conventional digital optical diagnostic tools, in which the image received at a digital sensor typically requires further focusing, either manually by a user or via an automatic mechanism.

Head portion 12004 and hand-holdable portion 12002 may be formed as modular components of instrument 12000, such that hand-holdable portion 12002 may be compatible for use with a variety of types of replaceable, removable optical examination head portions 12004 of the present invention. In an alternative possible embodiment of the present invention, hand-holdable portion 12002 may be configured so as to be capable of supporting more than one type of optical examination head portion 104 simultaneously thereupon. Alternatively, hand-holdable portion 12002 may be a dedicated handle portion adapted for use with a single type of optical examination head portion 12004 and optionally unitarily formed therewith.

An elongate optical passage 12034 is preferably formed along and within head portion 12004. Optical passage 12034 preferably has a first proximal end 12036 positioned proximal to a user's eye when instrument 12000 is in use and a second distal end 12038 positioned proximal to the ear during examination thereof. Distal end 12038 preferably comprises a distal opening 12040. Opening 12040 is preferably enclosed by a distal insertion portion 12044 insertable into the ear. Distal insertion portion 12044 maybe embodied as a tip element 12044 such as a speculum having a distal opening.

Speculum 12044 may be a disposable element or a reusable element integrally formed with head portion 12004. Speculum 12044 is preferably adapted for insertion in the ear of a patient during examination thereof, as is well known in the art. Head portion 12004 may optionally additionally include an insufflator port (not shown) into which air may be blown in order to apply pressure to the ear drum, as is well known in the art.

Head portion 12004 may include light sources for illuminating the field of view of the user during examination, such as a plurality of light sources 12052. Light sources 12052 may be embodied as LEDs, emitting light of one or more wavelengths suitable for illumination of the field of view of instrument 12000. By way of example only, LEDs 12052 may emit UV and/or blue light.

An array of optical elements 12060 is preferably housed in optical passage 12034. Array of optical elements 12060 is preferably but not necessarily linearly arranged. Array of optical elements 12060 preferably includes a first train of lenses 12062 and a second train of lenses 12064 spaced apart from first train of lenses 12062 and optically aligned therewith. Head portion 12004 further preferably includes a beam splitter 12080, preferably located anterior to array of optical elements 12060 and optically aligned therewith.

It is appreciated that array of optical elements 12060 and beam splitter 12080 comprise a particularly preferred embodiment of optical examination and non-digitized viewing optics 12028 of optical head portion 12004. Array of optical elements 12060, beam splitter 12080 and distal opening 12040 are preferably aligned along a first common optical pathway 12200 extending along optical passage 12034. First common optical pathway 12200 may be a linear pathway, as illustrated herein, or may be non-linear pathway, in which case array of optical elements 12060 may be arranged in a non-linear fashion therealong and may include alternative and/or additional optical elements for diverting a direction of light passing therethrough.

In operation of head portion 12004, speculum 12044 is preferably inserted in the ear of a patient to be examined, illumination of which is provided by LEDs 12052. Light reflected or scattered from the tympanic membrane of the ear of a patient enters head portion 12004 through distal opening 12040 and propagates towards beam splitter 12080.

Light impinging on beam splitter 12080 is preferably split in two directions by beam splitter 12080. A first portion of the light is preferably transmitted through beam splitter 12080 and continues to travel through optical passage 12034 along optical pathway 12200. A second portion of the light is reflected by beam splitter 12080 in a direction that is angled with respect to first optical pathway 12200, so as to exit optical passage 12034. Here, by way of example, the second portion of light is seen to be deflected along a second optical pathway 12202, preferably but not necessarily in a direction generally perpendicular to first optical pathway 12200. Second optical pathway 12202 may be a linear pathway, as illustrated herein, or may be non-linear pathway, as is exemplified henceforth with reference to FIG. 14.

The first portion of light transmitted through beam splitter 12080 along first optical pathway 12200 is preferably received by first train of lenses 12062. First train of lenses 12062 is preferably operative to create an image of the target, for viewing as an intermediate image plane setup by second train of lenses 12064. Second train of lenses 12064 is preferably operative to receive the intermediate image produced by first train of lenses 12062 and create a focused image for viewing by the user. First train of lenses 12062 thus preferably functions as an eye-piece relay, for relaying an image to the eye-piece formed by second train of lenses 12064.

It is appreciated that the particular configuration, including number and shapes of lenses illustrated as comprising first and second trains of lenses 12062 and 12064 is illustrative only, and that first and second trains of lenses 12062 and 12064 may comprise a greater or fewer number of optical elements of varying shapes and sizes. Furthermore, the particular above-described configuration of head portion 12004 is exemplary only and may be modified by one skilled in the art. For example, head portion 12004 may be modified to function as an alternative type of opto-diagnostic head portion, rather than as an otoscope.

In use of instrument 12000, a user may insert speculum 12044 into the ear of a patient and look through proximal end 12036 to see a non-digitized image of the inner ear. The user may make slight adjustments to the location of the instrument in the ear in order for the desired features of the inner ear to be in focus on the user's eye. It is understood that once instrument 12000 is placed by the user in the desired location, an in-focus analogue image is preferably presented to the user, without requiring focusing adjustments to be made to the image or to the optical elements of optics 12028. Optical elements 12060 thus preferably do not comprise adjustable optical elements and instrument 12000, and particularly head portion 12004 thereof, preferably does not include any manual or electronic focusing mechanisms.

It is appreciated that first optical pathway 12200 thus constitutes a non-digital optical pathway, wherealong light emanating from the target is transmitted to a user, allowing the user to view a non-digitized image of the target.

Due at least to the unique arrangement of optical elements 12060 along first optical pathway 12200, the non-digitized image generated thereby is in focus on the user's eye when viewed by the user through second train of lenses 12064. The user may thus immediately interpret the non-digitized image without any additional focusing adjustments to the image being required.

The second portion of light reflected by beam splitter 12080 along second optical pathway 12202 is preferably incident upon image digitization circuitry 122, preferably comprising digital sensor 1300. It is appreciated that second optical pathway 12202 thus constitutes a digital optical pathway, wherealong light emanating from the target is transmitted to digital sensor 1300, thus facilitating the formation of a digitized image of the target.

The second portion of light reflected by beam splitter 12080 may be received by a lens system 12300, which lens system preferably relays and focuses the received light upon digital sensor 1300. Here, by way of example, the lens system 12300 is shown to be comprise multiple lenses including a first group of lenses 12302, a second group of lenses 12304 and a third lens 12306. First group of lenses 12302, second group of lenses 12304 and third lens 12306 are preferably aligned along second optical pathway 12202 with digital sensor 1300.

First group of lenses 12302 is preferably functional to create an image of the target, which image is not necessarily appropriately sized for receipt by digital sensor 1300. Second group of lenses and third lens 12304 and 12306 are preferably functional to resize the image produced by first group of lenses 12302 and relay the resized image to digital sensor 1300. It is appreciated that second and/or third lenses 12304 and 12306 may be obviated, in the case that first group of lenses 12302 produces an appropriately sized image for receipt by digital sensor 1300.

It is appreciated that the image received by digital sensor 1300 is in focus on digital sensor 1300, such that additional focusing adjustments in order to further focus the image are preferably largely or entirely unnecessary. The need for additional focusing elements and/or mechanisms associated with digital sensor 1300 is thus advantageously obviated. Correspondingly, lens system 12300 need not comprise adjustable focusing elements or associated focusing mechanisms, in order to focus the image produced on digital sensor 1300.

It is understood that instrument 12000 thus exhibits light propagation and image formation along two separate optical paths, namely a first non-digital optical path represented by first non-digital optical pathway 12200 and a second digital optical path represented by second digital optical pathway 12202, optical components along the first and second paths being arranged so as to produce respective focused analogue and digitized images. Advantageously, due to the generation of respective focused analogue and digitized images, at least one and preferably both of the non-digital and digital optical paths does not require the inclusion of adjustable focusing mechanisms or elements therein. Preferably, the in-focus analogue and digitized images are produced simultaneously.

It is a particularly important feature of this embodiment of the present invention that lens system 12300 comprises multiple lenses relaying an image to image digitization, storage and transmission circuitry 120, rather than a single lens as described earlier in this specification, for example as with respect to instrument 100. Furthermore, image digitization circuitry 122, here embodied by way of example as digital sensor 1300, is preferably located at a significantly greater distance from the beam splitter 12080 than digital sensor 1300 with respect to beam splitter 180 in instrument 100, such that a physical length of the digital path and of digital pathway 12202 is significantly increased. By way of example, beam splitter 12080 may be located at a distance of between 1-25 cm, and particularly of between 7-15 cm, from a surface of digital sensor 1300, the separation between the beam splitter and sensor surface being measured along a generally straight path.

The inclusion of multiple lenses in the lens relay system 12300 interposed between the beam splitter and digital sensor, as well as the increased separation of the digital sensor from the beam splitter, in combination with the configuration of optics 12028, results in an increased focal depth of instrument 12000. This increases the range of locations at which a target may located with respect to instrument 12000 such that in-focus analogue and digitized images may be produced simultaneously.

For example, in the case that instrument 12000 is embodied as an otoscope, as illustrated in FIG. 12, a focal depth of 10 mm may be provided thereby, meaning that a target to be examined may lie at any location within a 10 mm locational range of a focal plane of instrument 12000 along non-digital pathway 12200 and remain in focus over substantially all of that locational range both in the analogue and digitized images produced by instrument 12000. An exemplary representative focal depth 12400 is schematically indicated in FIG. 12.

In the case that instrument 12000, and particularly head portion 12004 thereof, is embodied as an alternative type of opto-diagnostic instrument, such as a dermatoscope, opthalmoscope or general purpose examination instrument, the instrument may be operative to provide alternative focal depths. By way of example, a general purpose examination instrument constructed and operative in accordance with the present invention may have a focal depth of 30-100 cm, by way of example only.

It is appreciated that in the absence of multiple lenses in the lens relay system and/or in the case of reduced separation between the beam splitter and digital sensor, the range of locations at which a target is required to be located with respect to the instrument, in order to allow the instrument of the present invention to produce simultaneously focused digital and analogue images of the target, is more limited.

It is appreciated that an instrument of the present invention, such as instrument 100, 600, 800, 900 or 12000, may but does not necessarily need to include both multiple lenses in the lens relay system as well as an increased length of the digital pathway and increased distance between the beam splitter and the image digitization circuitry, in order for the instrument to exhibit an enhanced focal depth. By way of example, a single one of these features may be incorporated into an instrument of the present invention in order to increase the focal depth of the instrument.

The increased focal depth of an instrument of the present invention such as instrument 12000, whereby a target may be situated within a greater range of locations with respect to the instrument and remain in focus in both analogue and digital images over that range, allows a user greater flexibility in use of the instrument and reduces the sensitivity of both the analogue and digital images produced by the instrument to movement of the target.

Digital sensor 1300 may be cooperatively coupled to digital sensor board 1308. Digital sensor 1300 in combination with sensor board 1308 preferably comprises a digital camera for generating a digitized image of the target. The digitized image of the target may be a still image or may be a video frame forming a component of a digital video. Subsequent processing of the digital image or video produced at digital sensor 1300 is as explained with reference to FIGS. 4A, 4B, 5 and 11.

Lens system 12300 may be partially located in head portion 12004 and partially located in handle portion 12002, as illustrated in FIG. 12. Alternatively, lens system 12300 may be redistributed between head and handle portions 12004 and 12002 as shown in FIG. 13, in which an instrument 13000 is illustrated, generally resembling instrument 12000 but with lens system 12300 rearranged between head and handle portions 12004 and 12002.

Figure 13:
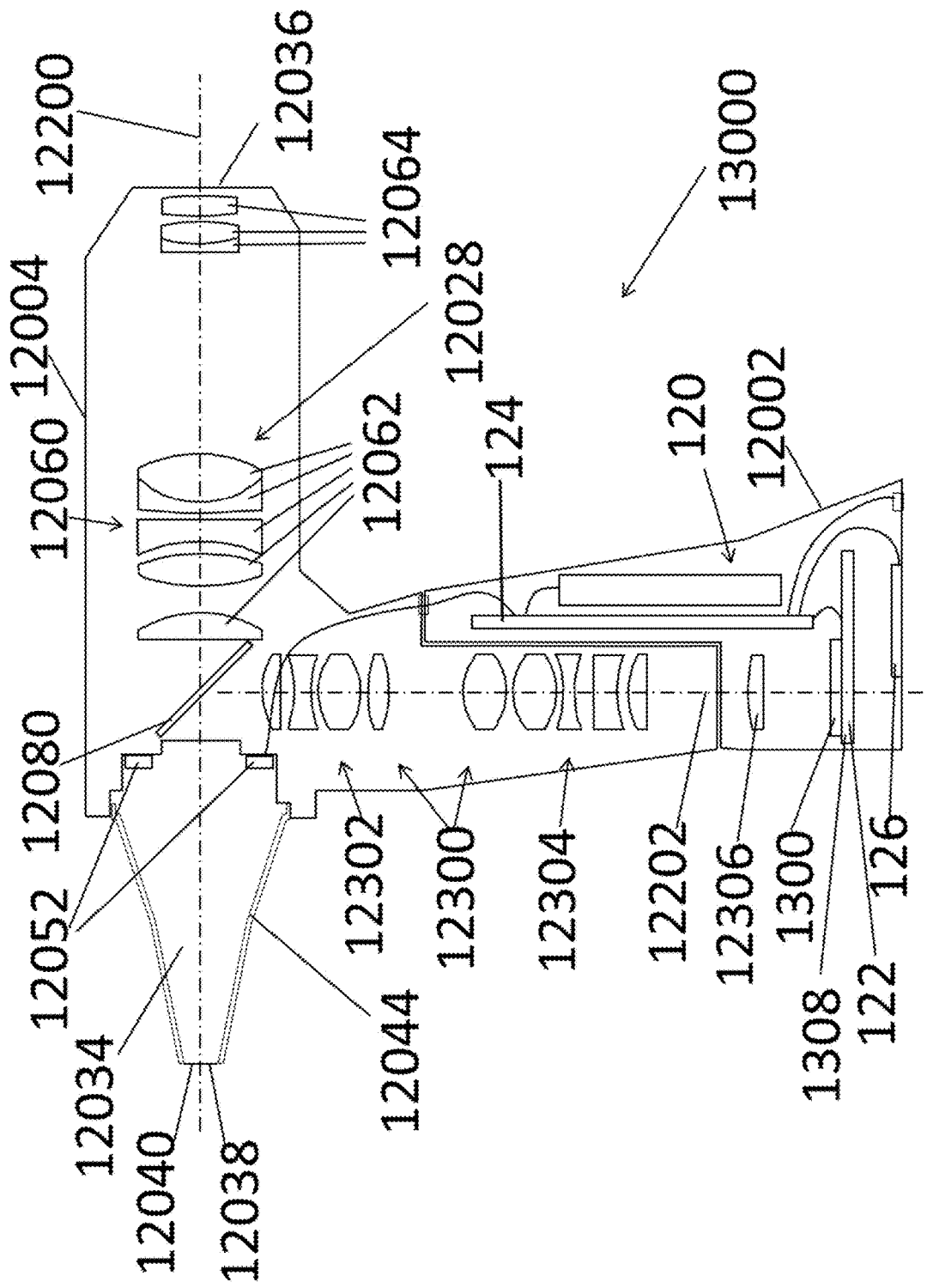
FIG. 13 is a simplified cross-sectional view illustration of a medical optical examination instrument constructed and operative in accordance with a still further preferred embodiment of the present invention.

Second optical pathway 12202 may be a linear pathway, as illustrated in FIGS. 12 and 13. Alternatively, second optical pathway 12202 may be a non-linear pathway, as illustrated in the case of an instrument 14000 shown in FIG. 14.

Figure 14:
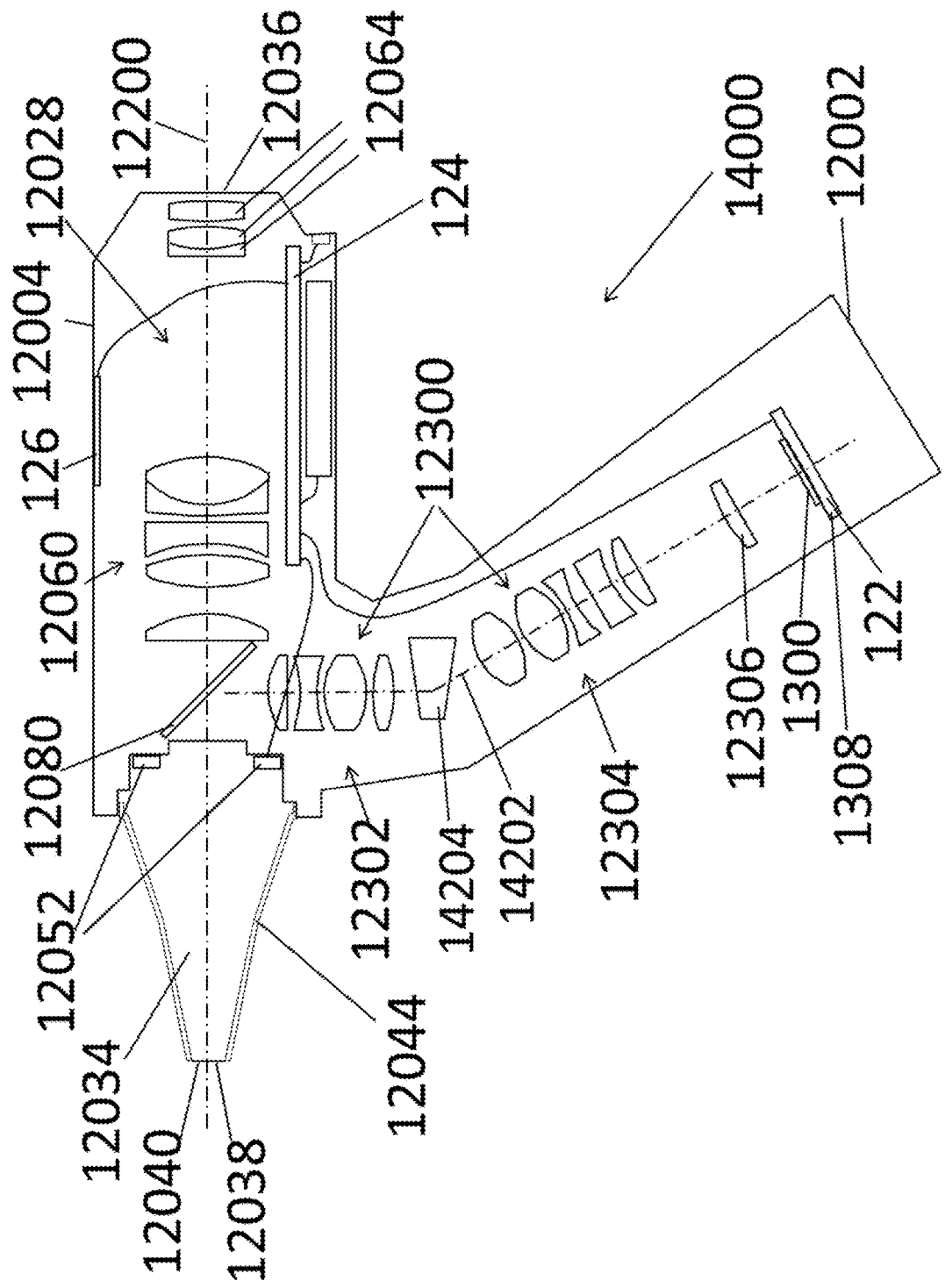
FIG. 14 is a simplified cross-sectional view illustration of a medical optical examination instrument constructed and operative in accordance with still another preferred embodiment of the present invention.

Turning now to FIG. 14, it is seen that instrument 14000 preferably includes a non-linear second optical pathway 14202, in contrast to the linear second optical pathway 12202 of instrument 12000. The provision of a non-linear digital pathway in the instrument of the present invention may be advantageous, for example in enhancing the ease of use of the instrument.

In order to provide a bent second optical pathway 14202, lens system 12300 may be modified so as to include alternative and/or additional optical components for diverting a direction of light passing therethrough. Here, by way of example, lens system 12300 is shown to be modified by the introduction of an additional lens 14204 inserted within lens system 12300. Lens 14204 preferably diverts a direction of light propagating therethrough so as to create an angular bend in second optical pathway 14202. Lenses of lens system 12300 may be located along bent second optical pathway 14202 such that lens system 12300 is not necessarily linearly arranged. Here, by way of example, second group of lenses and third lens 12304 and 12306 and digital sensor 1300 are shown to be angled with respect to first group of lenses 12302.

Handle portion 12002 may be integrally formed with head portion 12004 of instrument 14000, such that instrument 14000 comprises a unitary body, as illustrated herein. Alternatively, handle and head portions 12002 and 12004 may be formed as separate elements.

Image digitization, storage and transmission circuitry 122, 124, 126 may be distributed between handle and head portions 12004 and 12002, for example as shown herein, wherein image digitization circuitry 122 is located in handle 12002 and image storage and transmission circuitry 124, 126 is located in head portion 12004. Alternatively, image digitization, storage and transmission circuitry 120 may be included in at least one of head portion 12004 and handle portion 12002 in any suitable arrangement.

It will be appreciated by persons skilled in the art that the present invention is not limited by what has been particularly claimed hereinbelow. Rather, the scope of the invention includes various combinations and subcombinations of the features described hereinabove as well as modifications and variations thereof as would occur to persons skilled in the art upon reading the forgoing description with reference to the drawings and which are not in the prior art.

The invention claimed is:

1. A multifunctional medical optical examination instrument comprising:
   a hand-holdable portion;
   at least an optical examination head portion mountable on said hand-holdable portion and including at least optical examination and non-digitized viewing optics;
   a beam splitter located in said head portion;
   a lens system, receiving light from said beam splitter and comprising multiple lenses which relay and focus said light onto a digital sensor, whereby an image of a target received by said digital sensor from said optical examination and non-digitized viewing optics is in focus on said digital sensor; and
   image storage and transmission circuitry receiving an output of said digital sensor and being included in at least one of said hand-holdable portion and said at least optical examination head portion,
   said image storage and transmission circuitry being operative to receive said output of said digital sensor at least partially simultaneously with said image being viewable by a user via said optical examination and non-digitized viewing optics,
   said image viewable by said user via said optical examination and non-digitized viewing optics and said image received by said image storage and transmission circuitry each being in focus, without requiring focusing adjustments, said optical examination and non-digitized viewing optics being configured such that said image received by said image storage and transmission circuitry and said image viewable by said user via said optical examination and non-digitized viewing optics are at least partially simultaneously in focus when the target is located at any one of a range of locations within a focal depth of the instrument.

2. A multifunctional medical optical examination instrument according to claim 1 and wherein said instrument has a focal depth of less than or equal to 100 mm.

3. A multifunctional medical optical examination instrument according to claim 1 and wherein:
   said head portion comprises an optical passage extending therethrough, said optical passage comprising a distal end defining a distal opening and a proximal end defining a proximal opening, said distal opening being adapted for positioning in proximity to said target to be examined, said proximal opening being adapted for positioning in proximity to an eye of said user, said beam splitter being located within said optical passage between said distal and proximal ends thereof; and
   said distal opening, said proximal opening and said beam splitter are mutually optically aligned along a first optical pathway and at least a part of said image storage and transmission circuitry and said beam splitter are mutually optically aligned along a second optical pathway, said first and second optical pathways being mutually angled.

4. A multifunctional medical optical examination instrument according to claim 3 and wherein:
   said at least part of said image storage and transmission circuitry comprises a digital sensor; and
   said beam splitter is separated from said digital sensor by a distance of between 1-25 cm.

5. A multifunctional medical optical examination instrument according to claim 1 and also comprising illumination sources located in said optical examination head portion.

6. A multifunctional medical optical examination instrument according to claim 1 and wherein:
   said image comprises at least one of a digital still image and a digital video frame; and
   said image storage and transmission circuitry is operative to store said image.

7. A multifunctional medical optical examination instrument according to claim 6 and wherein:
   said instrument is connectable to an external computing device;
   said image storage and transmission circuitry is operative to transfer said image to said external computing device; and
   said image storage and transmission circuitry is operative to perform live video streaming of said image to said external computing device in real time.

8. A multifunctional medical optical examination instrument according to claim 7 and wherein said transfer is wireless.

9. A multifunctional medical optical examination instrument according to claim 8 and wherein said image storage and transmission circuitry comprises at least one antenna.

10. A multifunctional medical optical examination instrument according to claim 7 and wherein said external computing device comprises a non-transitory computer readable medium having stored thereupon computer instructions including code segments having the following functionalities:
    image processing functionality, for receiving and processing said image generated by said image storage and transmission circuitry;
    image display functionality for displaying said image processed by said image processing functionality;
    image capture functionality for capturing said image displayed by said image display functionality; and
    image management functionality for managing said image captured by said image capture functionality.

11. A multifunctional medical optical examination instrument according to claim 10 and also comprising remote control functionality for remote control of said image storage and transmission circuitry.

12. A multifunctional medical optical examination instrument according to claim 1 and wherein:
    said optical examination head portion comprises an otoscope head portion; and
    said image storage and transmission circuitry is arranged to receive an image from at least a portion of said at least optical examination and non-digitized viewing optics of said otoscope head portion, when said otoscope head portion is mounted on said hand-holdable portion.

13. A multifunctional medical optical examination instrument according to claim 1 and wherein:
    said optical examination head portion comprises a dermatoscope head portion; and
    said image storage and transmission circuitry is arranged to receive an image from at least a portion of said at least optical examination and non-digitized viewing optics of said dermatoscope head portion, when said dermatoscope head portion is mounted on said hand-holdable portion.

14. A multifunctional medical optical examination instrument according to claim 1 and wherein:

said optical examination head portion comprises an ophthalmoscope head portion; and said image storage and transmission circuitry being arranged to receive an image from at least a portion of said at least optical examination and non-digitized viewing optics of said ophthalmoscope head portion, when said ophthalmoscope head portion is mounted on said hand-holdable portion.

15. A multifunctional medical optical examination instrument set comprising:

a multifunctional medical optical examination instrument according to claim 1; and a plurality of head portions, each of said plurality of head portions comprising one of an otoscope head portion, a dermatoscope head portion, an ophthalmoscope head portion a general purpose examination head portion, said plurality of head portions being interchangeably and replaceably mountable on said hand-holdable portion; and wherein said optical examination head portion comprises one of said plurality of head portions.

16. A multifunctional medical optical examination instrument according to claim 1 and wherein:

said lens system comprises a first group of lenses, a second group of lenses and a third group of lenses aligned along each optical pathway with said digital sensor.

17. A multifunctional medical optical examination instrument according to claim 16 and wherein said first group of lenses is operative to create an initial image and said second and third groups of lenses are operative to resize said initial image and relay said image to said digital sensor.

18. A multifunctional medical optical examination instrument according to claim 1 and wherein:

said lens system is configured to enhance the focal depth of said instrument, thereby increasing a range of locations at which a target may be located with respect to said instrument such that in-focus non-digitized and digitized images of said target may be produced simultaneously.

19. A multifunctional medical optical examination instrument according to claim 1 and wherein:

said optical examination and non-digitized viewing optics do not comprise adjustable optical elements; and said instrument does not include any manual or electronic focusing mechanisms.

20. A multifunctional medical optical examination instrument comprising:

optical examination and non-digitized viewing optics providing an image of a target, said optical examination and non-digitized viewing optics including a beam splitter;

a lens system, receiving light from said beam splitter and comprising multiple lenses which relay and focus said light onto a digital sensor, whereby an image received by said digital sensor from said optical examination and non-digitized viewing optics is in focus on said digital sensor; and image storage and transmission circuitry receiving an output of said digital sensor at least partially simultaneously with said image being viewable by a user via said optical examination and non-digitized viewing optics, at least said optical examination and non-digitized viewing optics being configured such that said image received by said image storage and transmission circuitry and said image viewable by said user via said optical examination and non-digitized viewing optics are at least partially simultaneously in focus when said target is located at any one of a range of locations within a focal depth of said instrument, said image received by said image storage and transmission circuitry and said image viewable by said user via said optical examination and non-digitized viewing optics are at least partially simultaneously in focus without requiring focusing adjustments to said optical examination and non-digitized viewing optics and to said lens system.

21. A multifunctional medical optical examination instrument according to claim 20 and wherein said optical examination and non-digitized viewing optics also comprise:

a first train of lenses spaced apart from said beam splitter and operative to form an intermediate image of said target; and a second train of lenses spaced apart from said first train of lenses, said second train of lenses being operative to receive said intermediate image and focus said intermediate image to form said image of said target viewable by said user.

22. A multifunctional medical optical examination instrument according to claim 21 and wherein:

said image storage and transmission circuitry comprises a digital sensor;

said digital sensor and said beam splitter are mutually optically aligned along an optical pathway; and said digital sensor is spaced apart from said beam splitter along said optical pathway by a distance of 1-25 cm.

23. A multifunctional medical optical examination instrument according to claim 21 and wherein:

said image storage and transmission circuitry comprises a digital sensor;

said digital sensor and said beam splitter are mutually optically aligned along an optical pathway; and said optical pathway is linear.

24. A multifunctional medical optical examination instrument according to claim 21 and wherein:

said image storage and transmission circuitry comprises a digital sensor;

said digital sensor and said beam splitter are mutually optically aligned along an optical pathway; and said optical pathway is non-linear.

25. A multifunctional medical optical examination instrument according to claim 20 and wherein said focal depth is less than or equal to 100 mm.

* * * * *